United States Patent
Yousfi et al.

(10) Patent No.: US 12,266,101 B2
(45) Date of Patent: Apr. 1, 2025

(54) SYSTEMS AND METHODS FOR ANALYSIS OF PROCESSING ELECTRONIC IMAGES WITH FLEXIBLE ALGORITHMIC PROCESSING

(71) Applicant: PAIGE.AI, Inc., New York, NY (US)

(72) Inventors: Razik Yousfi, Brooklyn, NY (US); Peter Schueffler, Munich (DE); Thomas Fresneau, Oro Valley, AZ (US); Alexander Tsema, New York, NY (US)

(73) Assignee: Paige.AI, Inc., New York, NY (US)

( * ) Notice: Subject to any disclaimer, the term of this patent is extended or adjusted under 35 U.S.C. 154(b) by 414 days.

(21) Appl. No.: 17/729,041

(22) Filed: Apr. 26, 2022

(65) Prior Publication Data

US 2022/0343499 A1 Oct. 27, 2022

Related U.S. Application Data

(60) Provisional application No. 63/179,852, filed on Apr. 26, 2021.

(51) Int. Cl.
*G06T 7/00* (2017.01)
*G06N 20/20* (2019.01)

(52) U.S. Cl.
CPC .......... *G06T 7/0012* (2013.01); *G06N 20/20* (2019.01); *G06T 2207/20081* (2013.01); *G06T 2207/30068* (2013.01); *G06T 2207/30081* (2013.01)

(58) Field of Classification Search
CPC ......... G06T 7/0012; G06T 2207/20081; G06T 2207/30068; G06T 2207/30081; G06N 20/20; G06N 20/00; G16H 30/20; G16H 30/40; G16H 10/60; G16H 50/70
See application file for complete search history.

(56) References Cited

U.S. PATENT DOCUMENTS

| 11,436,344 | B1 * | 9/2022 | Juch | G06F 16/2365 |
| 2013/0208966 | A1 * | 8/2013 | Zhao | G06Q 40/08 709/219 |
| 2016/0117521 | A1 * | 4/2016 | Spalka | H04L 63/061 713/171 |
| 2017/0126642 | A1 * | 5/2017 | Basin | H04L 9/302 |

(Continued)

FOREIGN PATENT DOCUMENTS

| CN | 112052027 A | * | 12/2020 | |
| WO | WO-2015066650 A1 | * | 5/2015 | G16H 10/20 |

*Primary Examiner* — Chan S Park
*Assistant Examiner* — Sebastian-Sy Vuchi Ngo
(74) *Attorney, Agent, or Firm* — Bookoff McAndrews, PLLC

(57) ABSTRACT

A method may process an electronic image corresponding to a medical sample associated with a patient. The method may include receiving a selection of one or more artificial intelligence (AI) algorithms, receiving one or more whole slide images of a medical sample associated with a patient, performing a task on the whole slide images, using the one or more selected AI algorithms, the whole slide images being stored in a first container, the whole slide images being originated from a first user, the task comprising determining a characteristic of the medical sample in the whole slide images, based on the characteristic of the whole slide image, generating metadata associated with the whole slide image, and storing the metadata in a second container.

17 Claims, 19 Drawing Sheets

(56) References Cited

U.S. PATENT DOCUMENTS

| | | | | |
|---|---|---|---|---|
| 2017/0308800 | A1* | 10/2017 | Cichon | G06N 20/00 |
| 2019/0073510 | A1* | 3/2019 | West | G06F 18/40 |
| 2019/0130081 | A1* | 5/2019 | Sambamurthy | G06V 30/224 |
| 2020/0160122 | A1* | 5/2020 | Lints | G06T 3/40 |
| 2020/0211189 | A1* | 7/2020 | Yip | G06V 20/69 |
| 2021/0074429 | A1* | 3/2021 | Singhal | G06V 20/698 |
| 2021/0157904 | A1* | 5/2021 | Bursell | G06F 12/1466 |
| 2021/0279475 | A1* | 9/2021 | Tusch | H04L 63/0861 |
| 2023/0254127 | A1* | 8/2023 | Bernat | H04L 9/0897 713/171 |
| 2023/0395253 | A1* | 12/2023 | Long | G16H 40/67 |

* cited by examiner

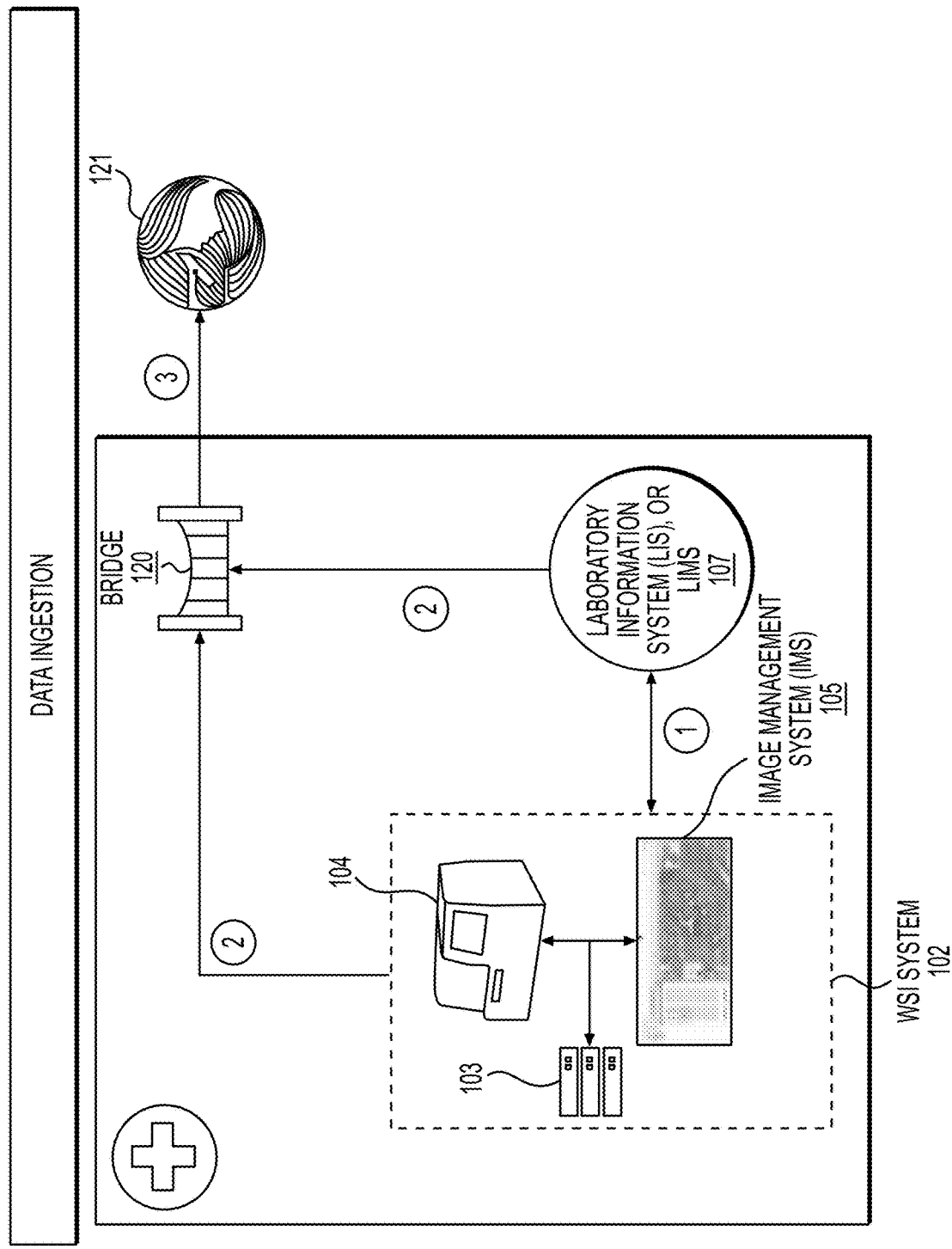

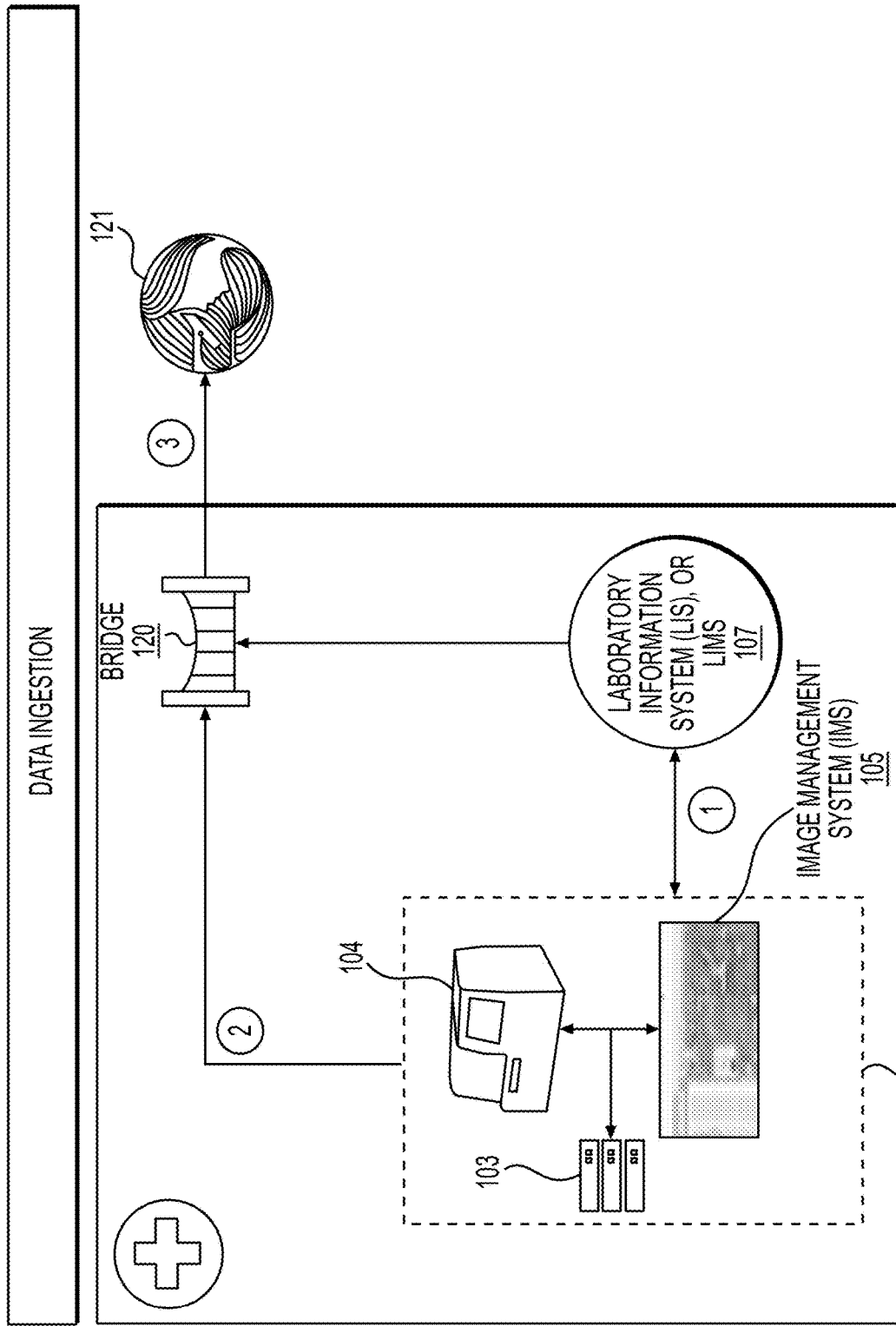

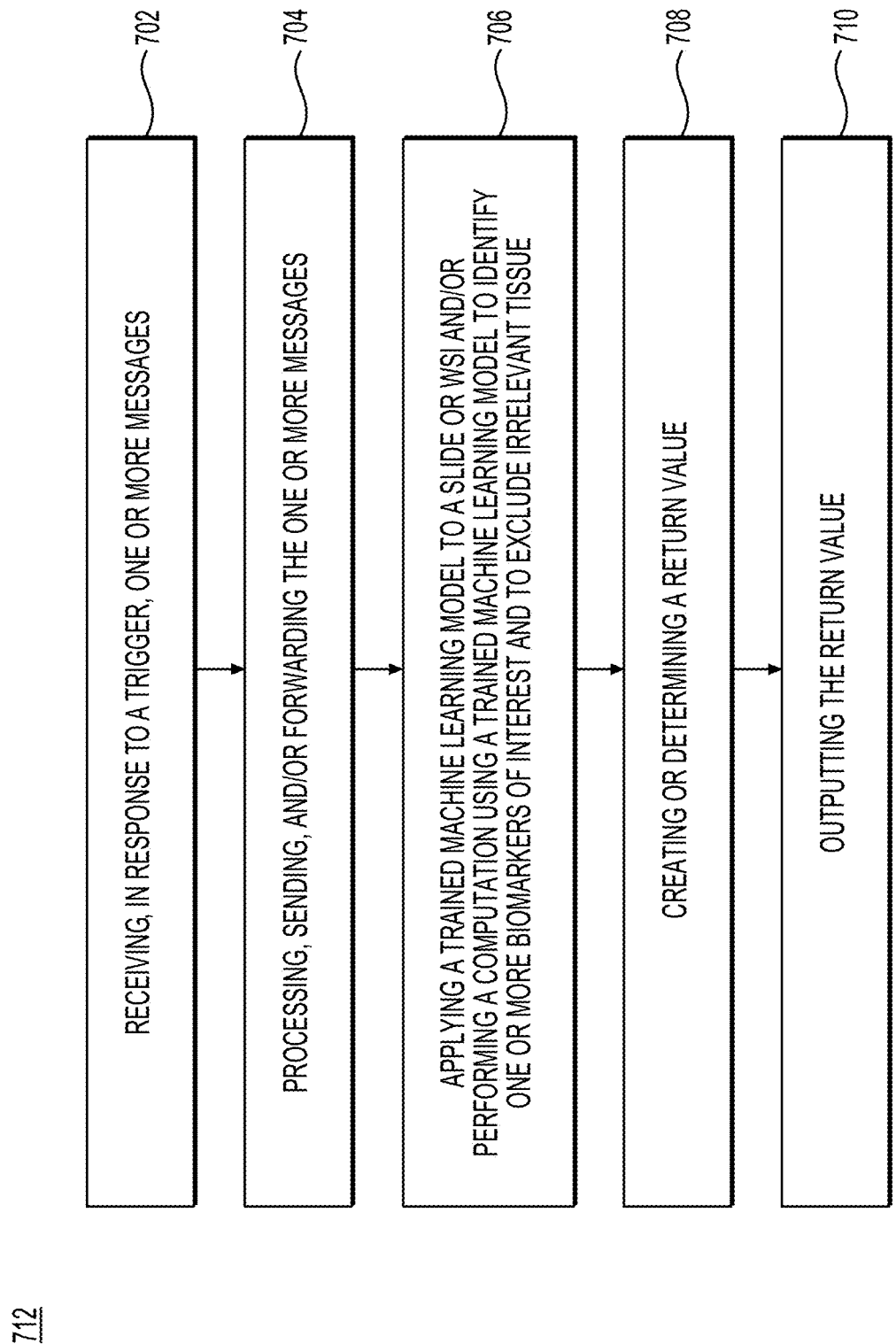

SYSTEMS AND METHODS FOR ANALYSIS OF PROCESSING ELECTRONIC IMAGES WITH FLEXIBLE ALGORITHMIC PROCESSING

RELATED APPLICATION(S)

This application claims priority to U.S. Provisional Application No. 63/179,852 filed Apr. 26, 2021, the entire disclosure of which is hereby incorporated herein by reference in its entirety.

FIELD OF THE DISCLOSURE

Various embodiments of the present disclosure pertain generally to computational pathology workflows for processing electronic images. More specifically, particular embodiments of the present disclosure relate to systems and methods for workflows using clinical-grade products for the treatment of cancer.

BACKGROUND

The process of using computers to assist pathologists is known as computational pathology. In the field of computational pathology, information security and data privacy are important considerations in ensuring that personal data and health-related information are protected.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic images corresponding to a medical sample associated with a patient and/or for selecting AI modules.

A method for processing an electronic image corresponding to a medical sample associated with a patient may include receiving a selection of one or more artificial intelligence (AI) algorithms, receiving one or more whole slide images of a medical sample associated with a patient, performing a task on the whole slide images, using the one or more selected AI algorithms, the whole slide images being stored in a first container, the whole slide images being originated from a first user, the task comprising determining a characteristic of the medical sample in the whole slide images, based on the characteristic of the whole slide image, generating metadata associated with the whole slide image, and storing the metadata in a second container.

The one or more selected AI algorithms may be among a plurality of AI algorithms available in a cloud computing environment.

At least one of the plurality of AI algorithms may have been developed by a second user, and at least another of the plurality of AI algorithms may have been developed by a third user different from the second user. The second user may be located in a different region than the third user.

The method may include selecting an AI algorithm among the plurality of AI algorithms to be the one or more selected AI algorithms. Selecting the AI algorithm may be based on a request indicating a type of task to be performed, a request indicating a type of metadata to be generated, a command for a particular AI algorithm, additional information or metadata associated with the stored whole slide image, one or more rules or policies received by the first user, one or more rules or policies associated with the AI algorithms among the plurality of AI algorithms, and/or one or more rules or policies received from one or more users, the one or more users having developed the AI algorithms among the plurality of AI algorithms.

The method may further include receiving a request, from a second user, to apply the selected AI algorithm to perform the task on the whole slide images.

The AI algorithm may intake supplemental information associated with the whole slide image. The supplemental information may include generic profile patient, patient history, related slide images, radiology data, molecular data, and/or clinical data.

The method may include determining one or more rules associated with the second container, generating a modified whole slide image and/or modified metadata by performing, based on the one or more rules associated with the second container: (i) removing data from the whole slide image and/or removing at least some of the metadata, and/or (ii) changing data from the whole slide image and/or changing at least some of the metadata, and outputting the modified whole slide image and/or the modified metadata to the user.

The method may include storing the whole slide image in a first container by performing automatic artificial-intelligence based ingestion of the whole slide image. The whole slide image may have been received from the first user.

The method may include receiving a request for at least one of the whole slide images from a device, comparing a location of the device to a location of the first user and/or patient, and determining, based on the compared location, whether sending the requested at least one whole slide image and the metadata to the device is permitted by a rule.

The method may include determining that sending the requested at least one whole slide image and the metadata to the device is permitted and providing the requested at least one whole slide image and the metadata to the device.

Determining that sending the requested at least one whole slide image to the device is permitted may include determining that the device is associated with a same institution as the first user. Applying the selected artificial intelligence algorithm to perform the task may be performed based on patient metadata associated with the patient.

Generating metadata may further comprise determining a heatmap. The heatmap may include a graphical prediction of a likelihood of an attribute in the medical specimen.

A system for processing an electronic image corresponding to a medical sample associated with a patient may include at least one memory storing instructions and at least one processor configured to execute the instructions to perform operations. The operations may include receiving a selection of one or more artificial intelligence (AI) algorithms, receiving one or more whole slide images of a medical sample associated with a patient, performing a task on the whole slide images, using the one or more selected AI algorithms, the whole slide images being stored in a first container, the whole slide images being originated from a first user, the task comprising determining a characteristic of the medical sample in the whole slide images, based on the characteristic of the whole slide image, generating metadata associated with the whole slide image, and storing the metadata in a second container.

The one or more selected AI algorithms may be among a plurality of AI algorithms available in a cloud computing environment. At least one of the plurality of AI algorithms may have been developed by a second user, and at least another of the plurality of AI algorithms may have been developed by a third user different from the second user.

The operations may include selecting an AI algorithm among the plurality of AI algorithms to be the one or more selected AI algorithms. Selecting the AI algorithm may be based on a request indicating a type of task to be performed, a request indicating a type of metadata to be generated, a command for a particular AI algorithm, additional information or metadata associated with the stored whole slide image, one or more rules or policies received by the first user, one or more rules or policies associated with the AI algorithms among the plurality of AI algorithms, and/or one or more rules or policies received from one or more users, the one or more users having developed the AI algorithms among the plurality of AI algorithms.

A non-transitory computer-readable medium may store instructions that, when executed by a processor, cause the processor to perform operations for processing an electronic image corresponding to a medical sample associated with a patient, the operations comprising receiving a selection of one or more artificial intelligence (AI) algorithms, receiving one or more whole slide images of a medical sample associated with a patient, performing a task on the whole slide images, using the one or more selected AI algorithms, the whole slide images being stored in a first container, the whole slide images being originated from a first user, the task comprising determining a characteristic of the medical sample in the whole slide images, based on the characteristic of the whole slide image, generating metadata associated with the whole slide image, and storing the metadata in a second container.

The one or more selected AI algorithms may be among a plurality of AI algorithms available in a cloud computing environment. At least one of the plurality of AI algorithms may have been developed by a second user, and at least another of the plurality of AI algorithms may have been developed by a third user different from the second user.

It is to be understood that both the foregoing general description and the following detailed description are exemplary and explanatory only and are not restrictive of the disclosed embodiments, as claimed.

BRIEF DESCRIPTIONS OF THE DRAWINGS

The accompanying drawings, which are incorporated in and constitute a part of this specification, illustrate various exemplary embodiments and together with the description, serve to explain the principles of the disclosed embodiments.

Figure 4B:
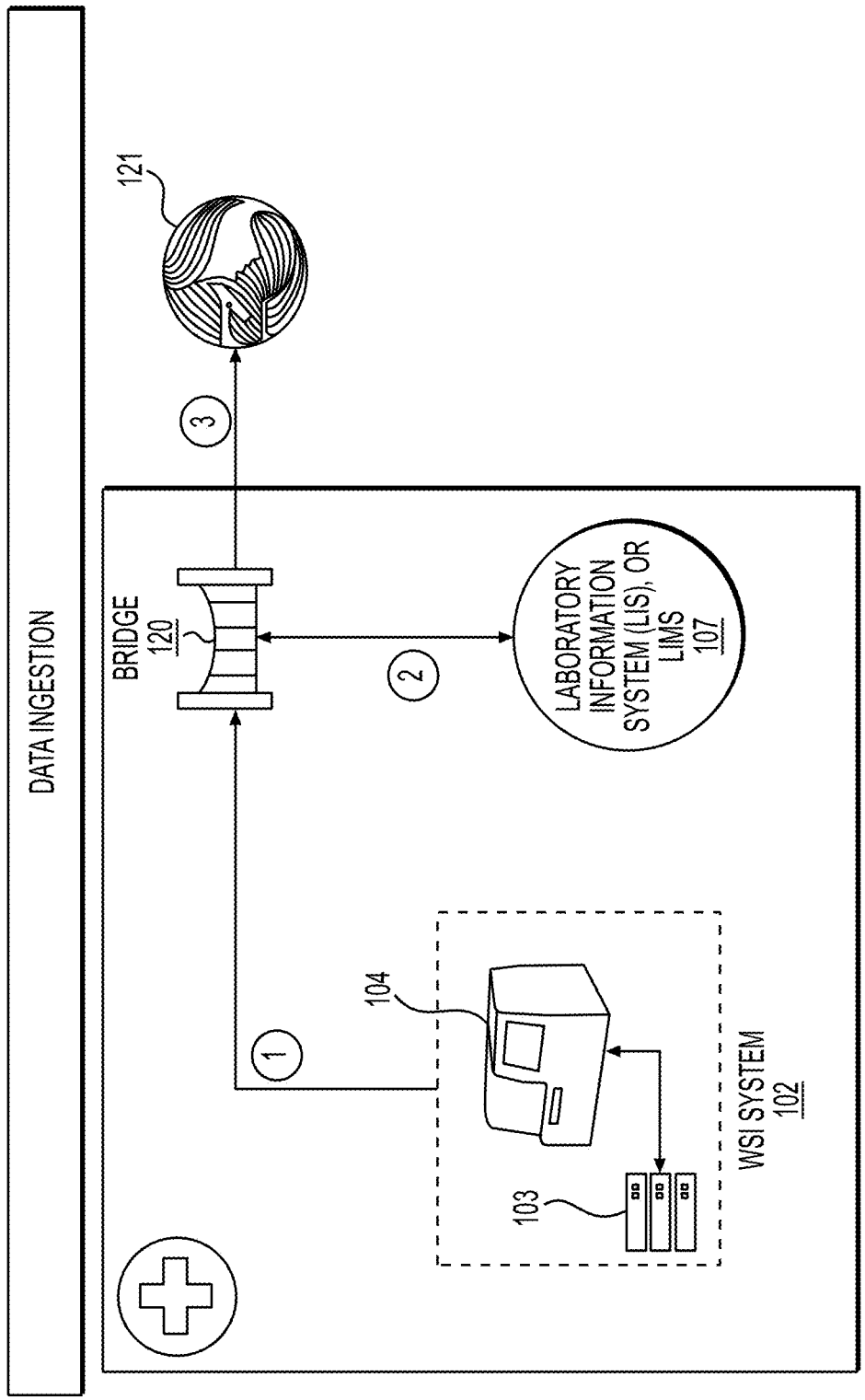

FIGS. 4A-C are exemplary architectures of a data ingestion appliance and integrations of the data ingestion appliance, according to exemplary embodiments.

Figure 5A:
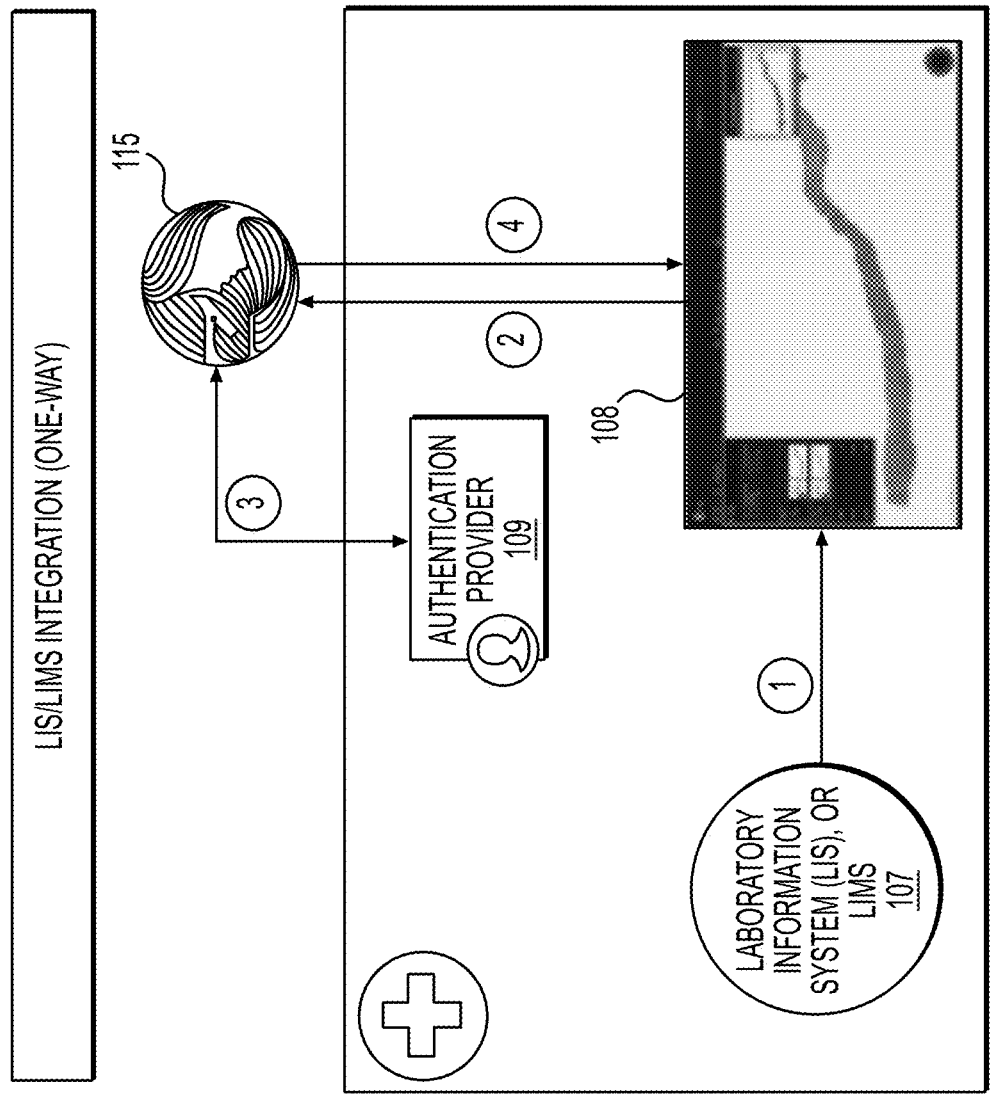
Figure 5B:
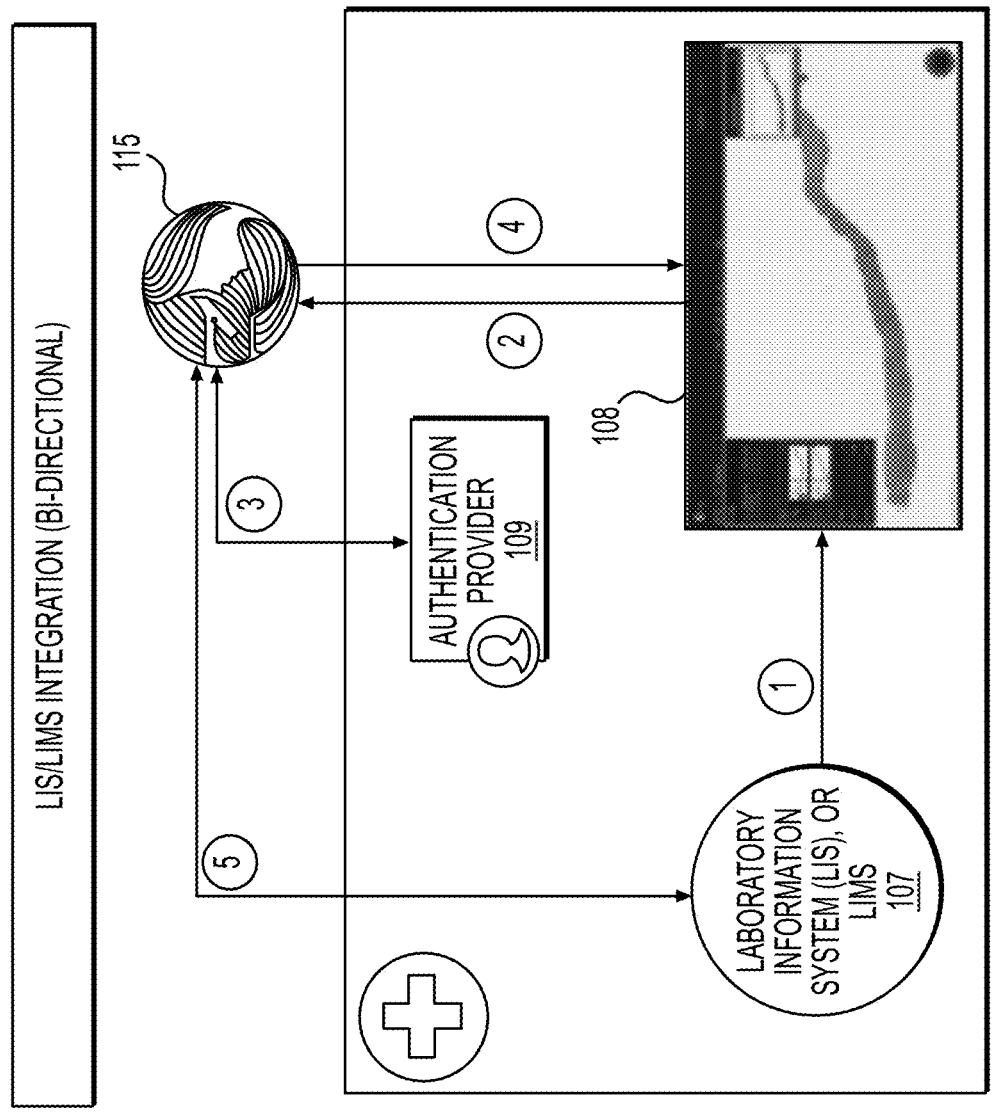
Figure 5C:
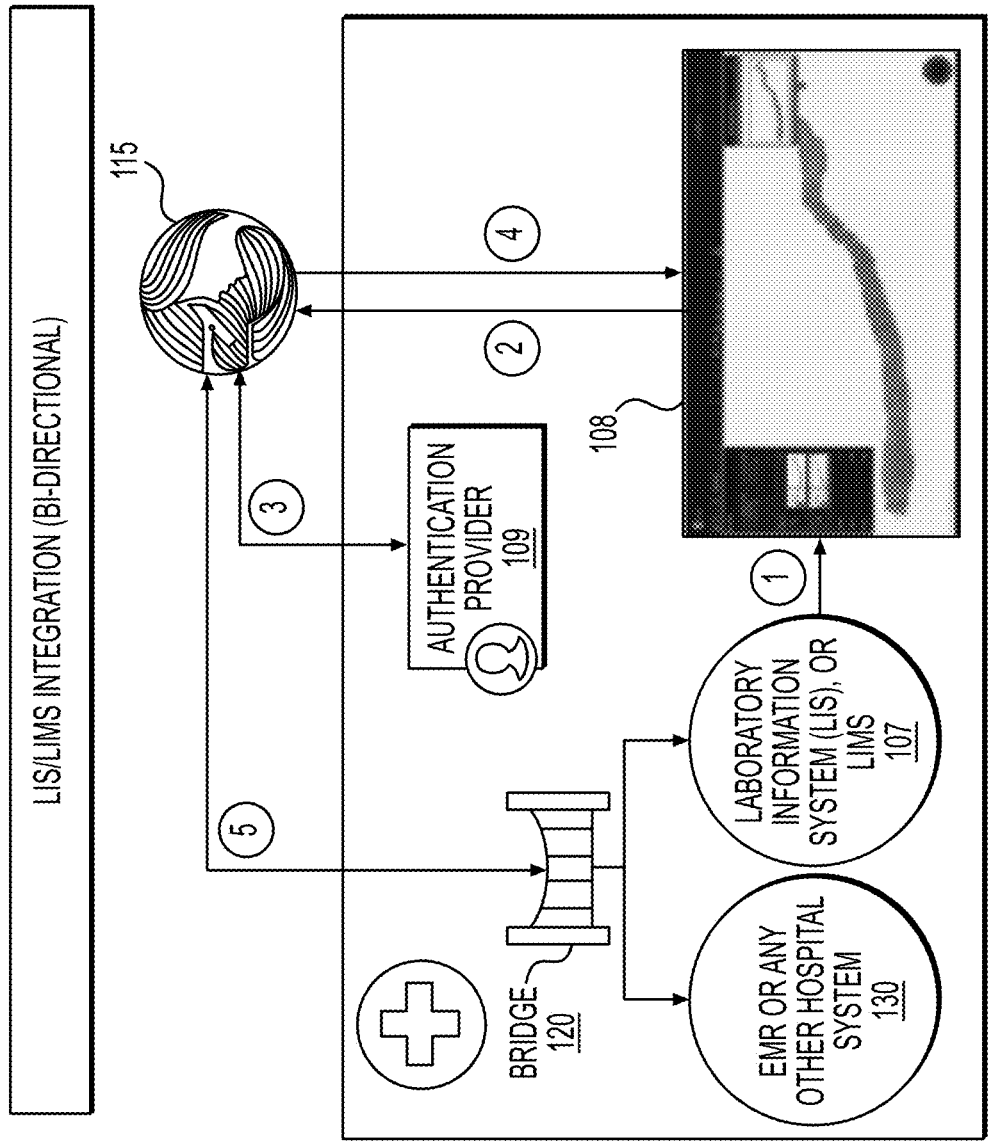

FIGS. 5A-C are exemplary architecture of a laboratory information system (LIS) and integration of the LIS, according to exemplary embodiments.

Figure 6:
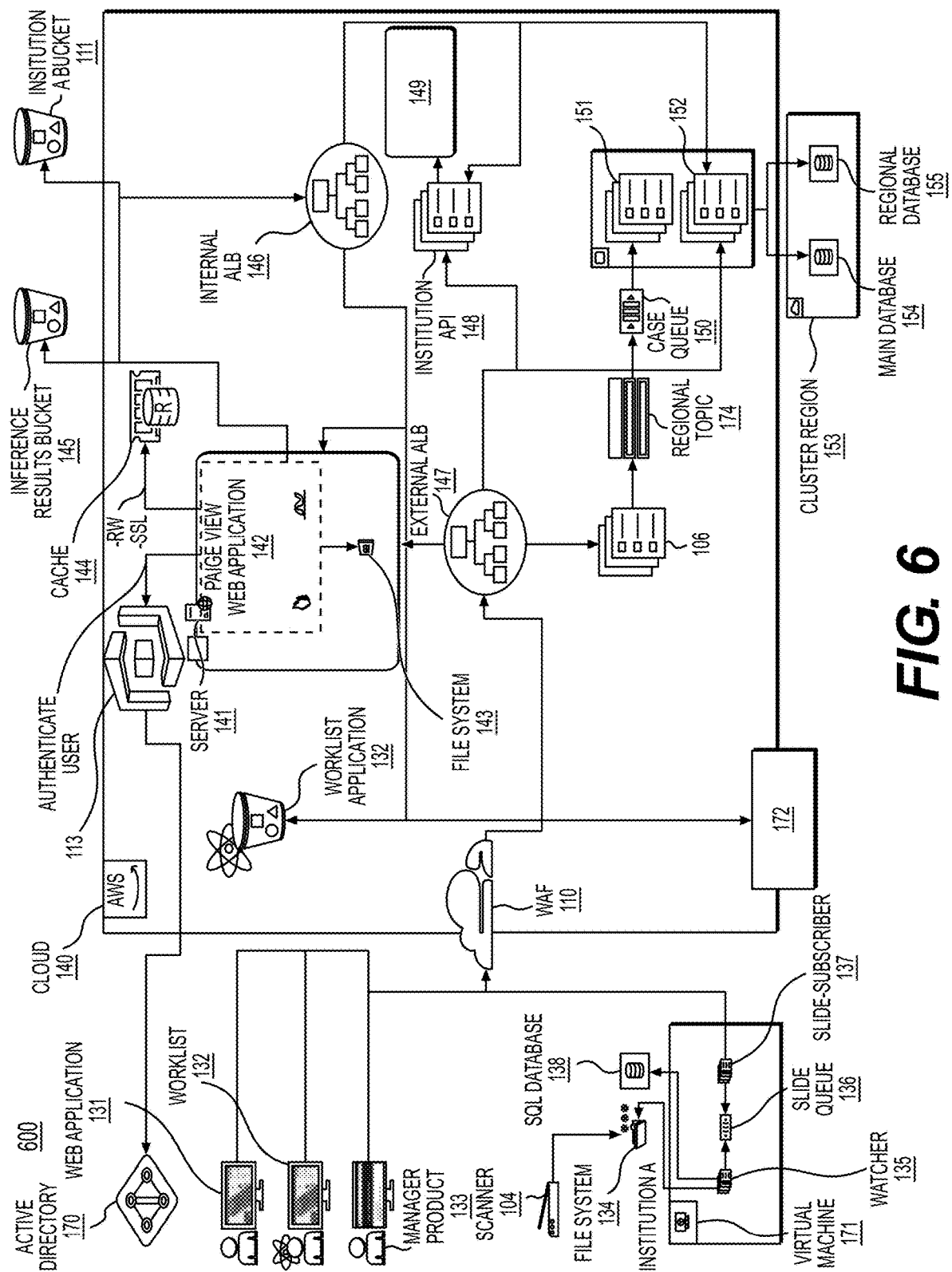

FIG. 6 is an exemplary architecture of a slide viewer, according to an exemplary embodiment.

Figure 7A:
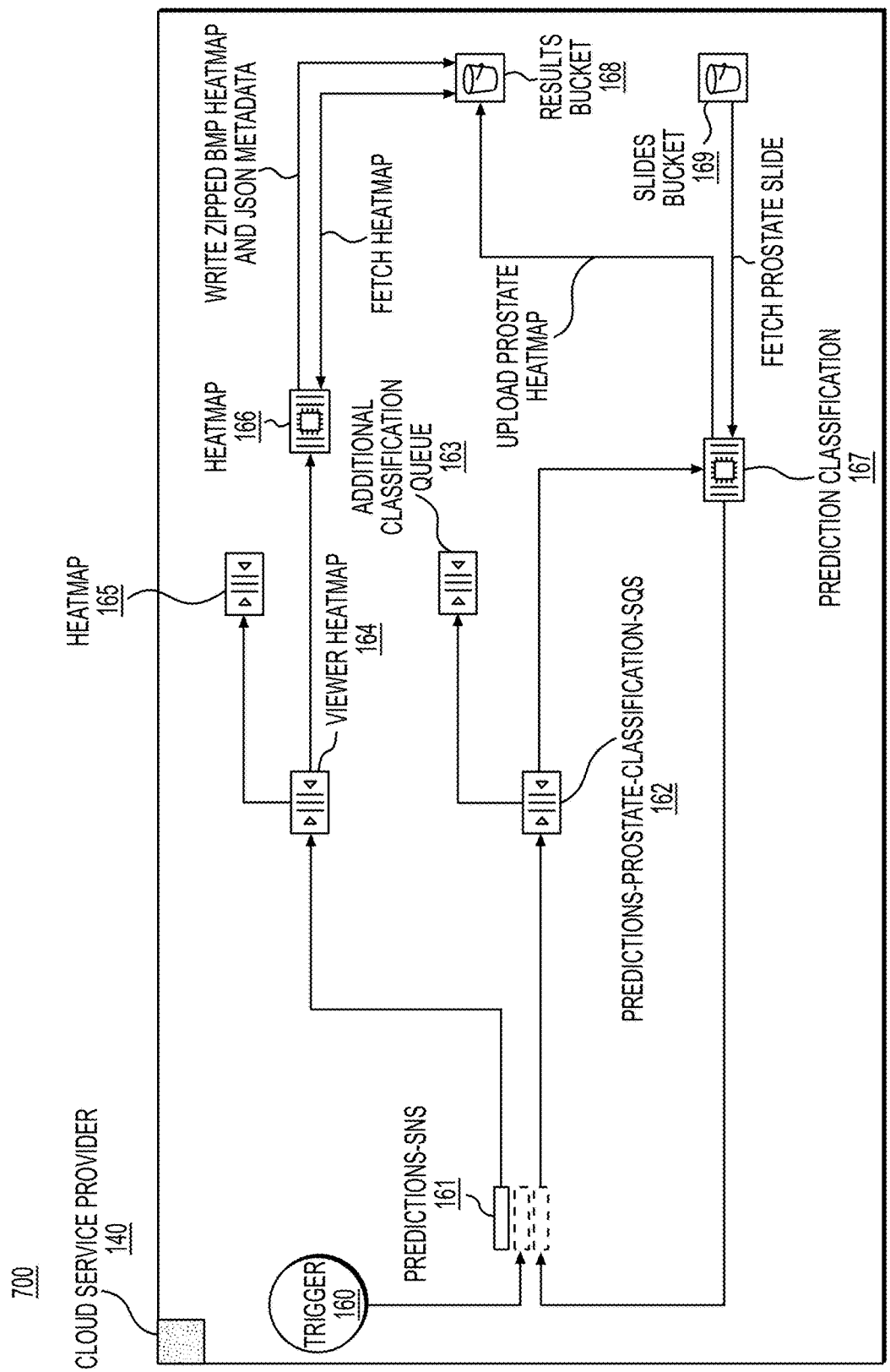

FIG. 7A is an exemplary architecture of an AI computer, according to an exemplary embodiment, and FIG. 7B is flowchart of an exemplary method using the exemplary architecture.

Figure 8:
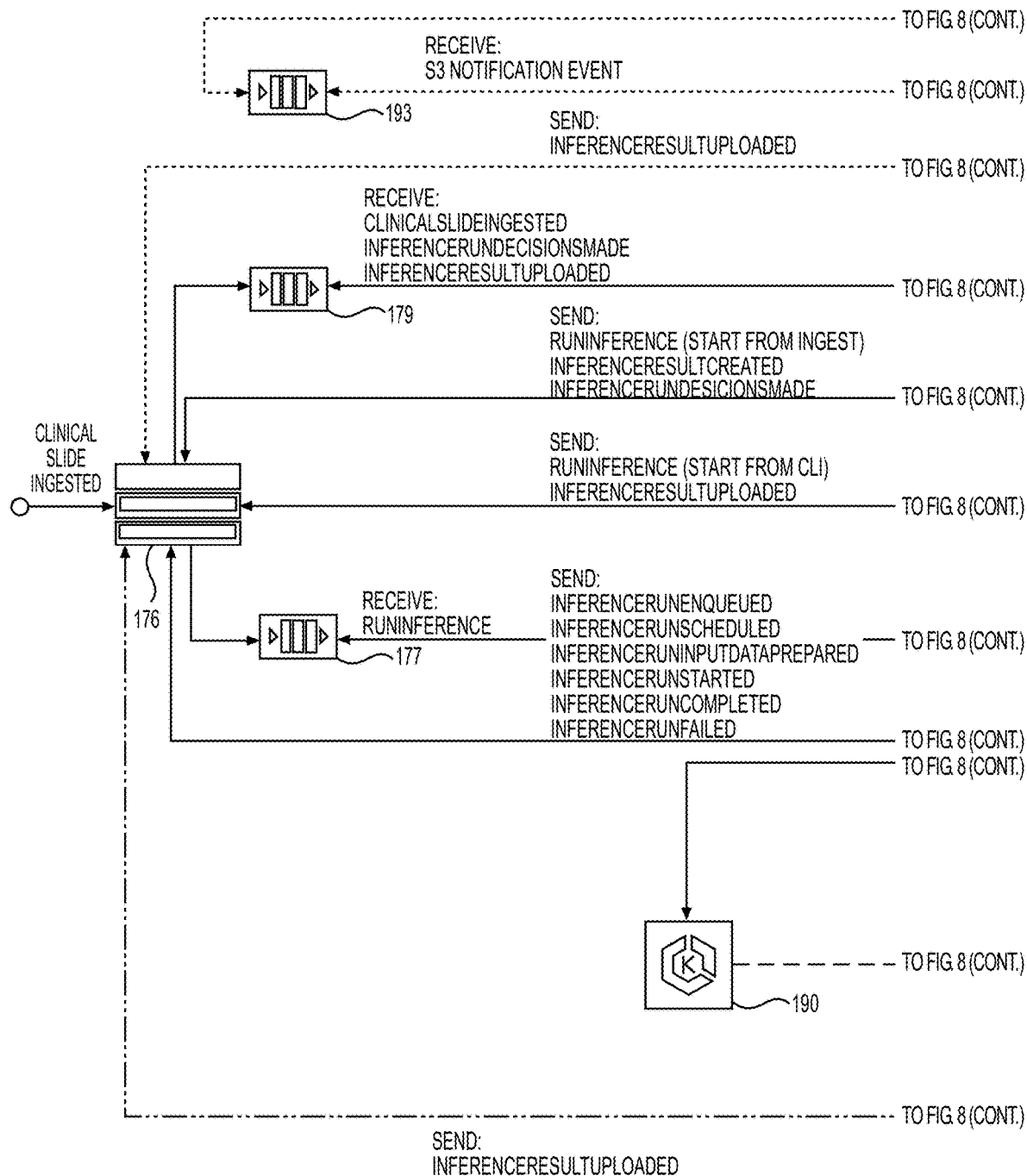
Figure 8:
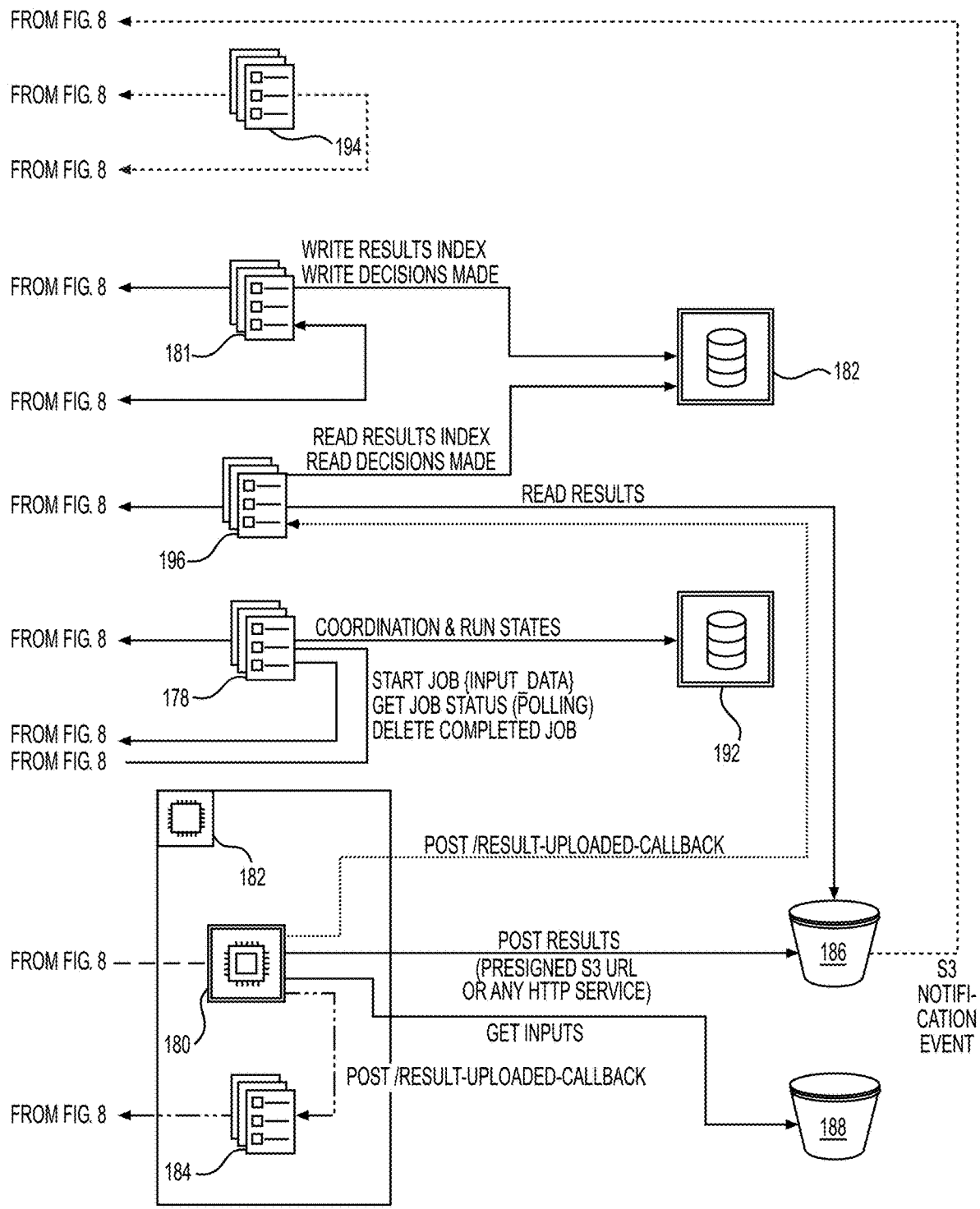

FIG. 8 is an exemplary inference architecture for use with the workflows and platforms architecture disclosed herein.

Figure 9:
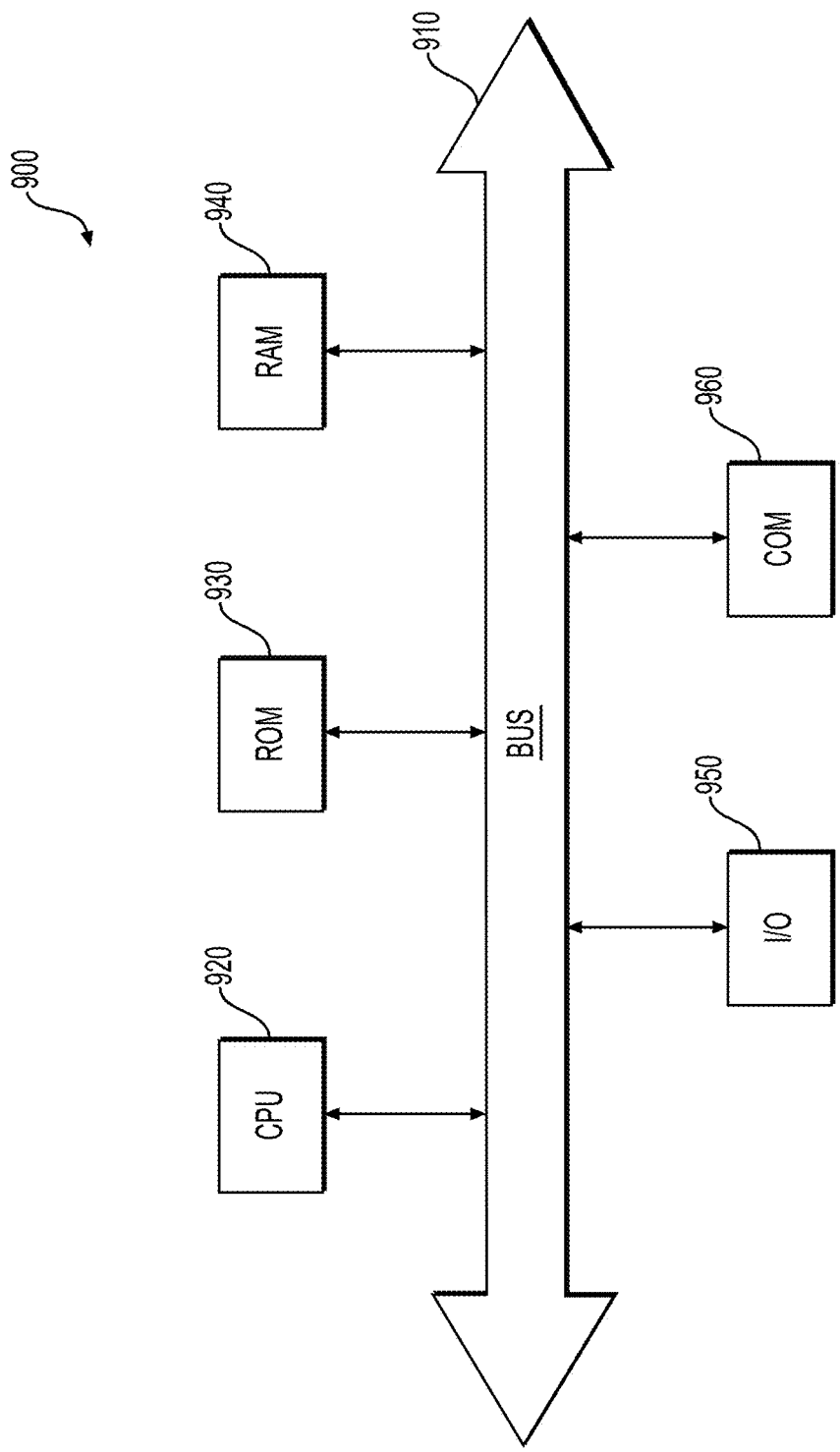

FIG. 9 depicts an example system that may execute techniques presented herein.

Figure 10A:
Figure 10B:
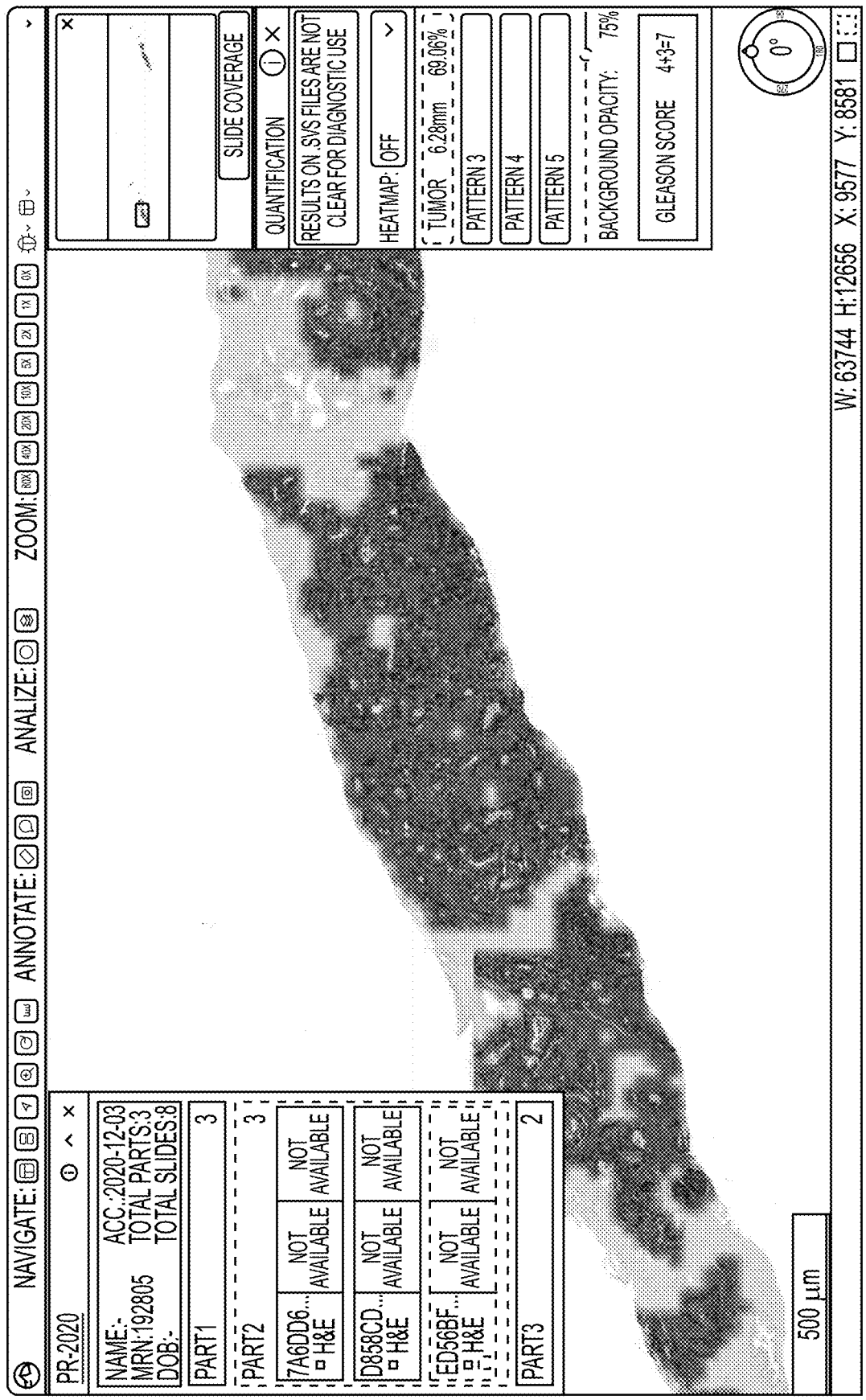
Figure 10C:
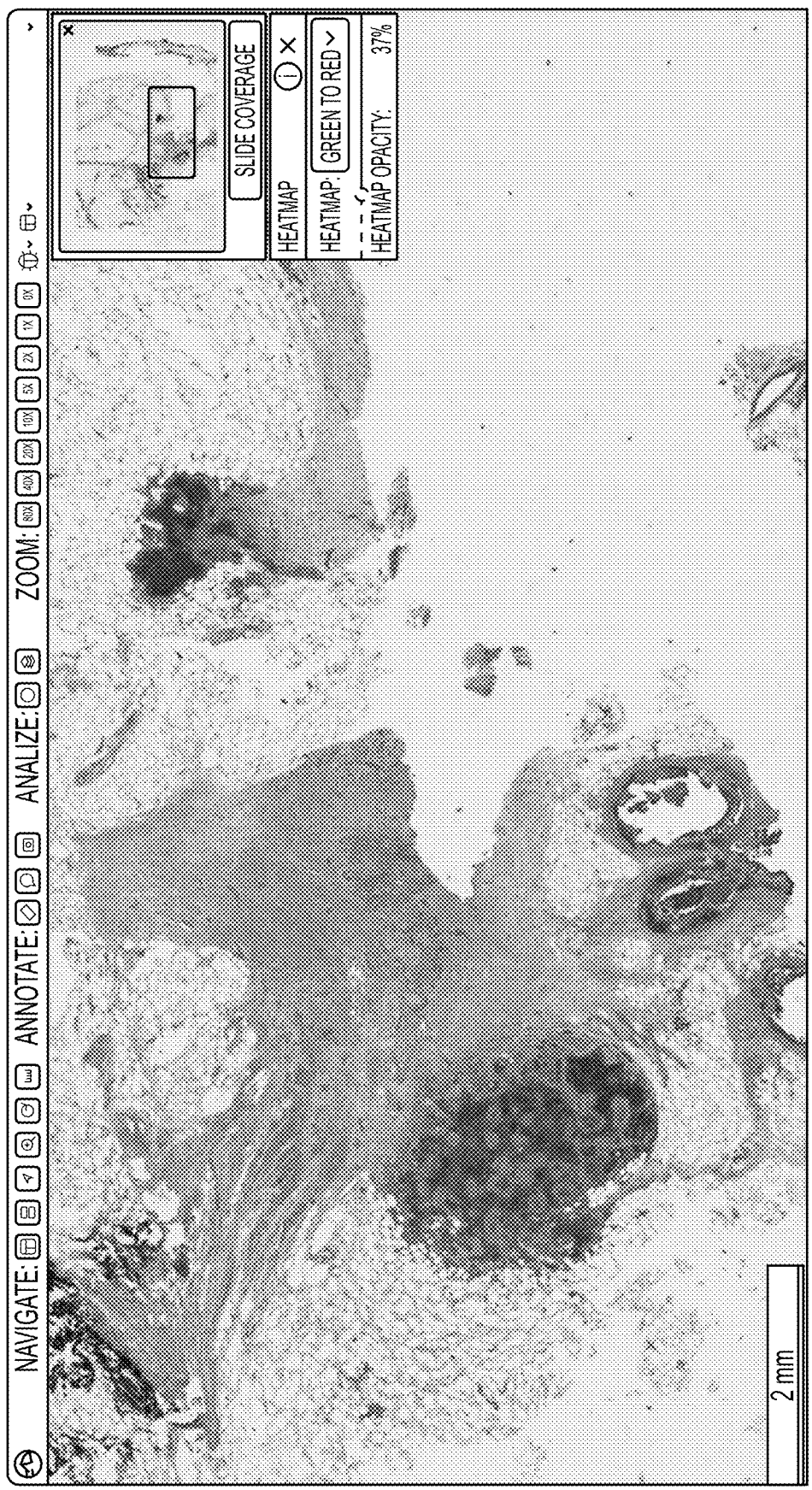

FIGS. 10A-C show exemplary outputs according to exemplary embodiments.

DESCRIPTION OF THE EMBODIMENTS

Reference will now be made in detail to the exemplary embodiments of the present disclosure, examples of which are illustrated in the accompanying drawings. Wherever possible, the same reference numbers will be used throughout the drawings to refer to the same or like parts.

Systems, devices, and methods disclosed herein provide computational pathology processes and workflows configured to be used with clinical-grade products that may transform the diagnosis and treatment of cancer. Computational pathology workflows described herein may improve diagnostic accuracy, reliability, efficiency, and accessibility. For example, a workflow of a device may detect slides as being suspicious for cancer, allowing pathologists to check their initial assessments before rendering a final diagnosis. Computational pathology processes and workflows of the present disclosure may use an integrated platform allowing the ingestion, processing, and viewing of digital pathology images via a web-browser, while being integrated with a Laboratory Information System (LIS), a customer-based diagnostic tool, or any other software development kit (SDK) application.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases, such as performing tests and analysis that are used to diagnose diseases. For example, tissue samples may be places onto slides to be viewed under a microscope by a pathologist or a physician that analyzes tissue samples to determine whether any abnormalities exist. Pathology specimens may be cut or sliced into multiple sections or cut levels, prepared as and/or placed on slides, and stained for a pathologist to examine and render a diagnosis.

When uncertain of a diagnostic finding on a slide, a pathologist may order additional cut levels, stains, or other tests to gather more information from the tissue. Technician(s) may then create new slide(s) which may contain the additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This process may significantly delay a final diagnosis that the pathologist renders. In addition, even after the delay, the pathologist may still not be certain that the new slide(s) will have information sufficient to render a diagnosis.

Pathologists may evaluate cancer and other disease slides in isolation. Systems, devices, and methods disclosed herein provide a platform to improve diagnosis of cancer and other diseases. The platform may integrate, for example, slide evaluation, tasks, image analysis, artificial intelligence (AI) (e.g., cancer detection AI), annotations, consultations, and recommendations in one workstation. Various exemplary user interfaces may be available in the platform, as well as AI tools that may be integrated into the platform to expedite and improve a pathologist's work.

For example, computers may analyze an image of a tissue sample to quickly identify whether additional information may be needed about a particular tissue sample and/or to highlight to a pathologist an area in which he or she should look more closely. Thus, the process of obtaining additional stained slides and tests may be done automatically before being reviewed by a pathologist. When paired with automatic slide segmenting and staining machines, a fully automated slide preparation pipeline may be provided. This automation may (1) minimize or reduce an amount of time wasted by a pathologist in determining that a slide is insufficient to make a diagnosis, (2) minimize or reduce an (average total) time from specimen acquisition to diagnosis by avoiding or reducing additional time between when additional tests are ordered and when they are produced, (3) reduce or minimize an amount of time per recut and an amount of material wasted by allowing recuts to be done while tissue blocks (e.g., pathology specimens) are in a cutting desk, (4) reduce or minimize an amount of tissue material wasted/discarded during slide preparation, (5) reduce or minimize a cost of slide preparation by partially or fully automating the procedure, (6) allow automatic customized cutting and/or staining of slides that would result in more representative and/or informative slides from samples, (7) allow higher volumes of slides to be generated per tissue block, contributing to more informed and/or precise diagnoses by reducing overhead of requesting additional testing for a pathologist, and/or (8) identify or verify correct properties (e.g., pertaining to a specimen type) of a digital pathology image, etc.

Computing methods used for computational pathology may include, but are not limited to, statistical analysis, autonomous or machine learning, and AI. AI may include, but is not limited to, deep learning, neural networks, classifications, clustering, and regression algorithms. Computational pathology may help save lives by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (i.e., benign) or abnormal (i.e., malignant). To assist pathologists in identifying and classifying nuclei, histological stains may be used to make cells visible. Many dye-based staining systems have been developed, including periodic acid-Schiff reaction, Masson's trichrome, nissl and methylene blue, and Hematoxylin and Eosin (H&E). For medical diagnosis, H&E is a widely used dye based method, with hematoxylin staining cell nuclei blue, eosin staining cytoplasm and extracellular matrix pink, and other tissue regions taking on variations of these colors.

In many cases, however, H&E-stained histologic preparations do not provide sufficient information for a pathologist to visually identify biomarkers that can aid diagnosis or guide treatment. In this situation, techniques such as immunohistochemistry (IHC), immunofluorescence, in situ hybridization (ISH), or fluorescence in situ hybridization (FISH), may be used. IHC and immunofluorescence involve, for example, using antibodies that bind to specific antigens in tissues to enable the visual detection of cells expressing specific proteins of interest, which can reveal biomarkers that are not reliably identifiable using H&E stained slides. ISH and FISH may be employed to assess a number of copies of genes or an abundance of specific RNA molecules, depending on the type of probes employed (e.g,. DNA probes for gene copy number and RNA probes for the assessment of RNA expression). If these methods fail to provide sufficient information to detect some biomarkers, genetic testing of the tissue may be used to confirm if a biomarker is present (e.g., overexpression of a specific protein or gene product in a tumor, amplification of a given gene in a cancer).

A digitized image may be prepared to show a stained microscope slide, which may allow a pathologist to manually view the image on a slide and estimate a number of stained abnormal cells in the image. However, this process may be time consuming and may lead to errors in identifying abnormalities, because some abnormalities are difficult to detect. Computational processes and devices may be used to assist pathologists in detecting abnormalities that may otherwise be difficult to detect.

For example, AI may be used to predict biomarkers (such as the overexpression of a protein and/or gene product, amplification, or mutations of specific genes) from salient regions within digital images of tissues stained using H&E and other dye-based methods. As another example, AI may be used to predict the presence of floaters (a type of abnormality) from individual regions within digital images of prepared tissue samples. The images of the tissues could be whole slide images (WSI) or images of tissue cores within microarrays or selected areas of interest within a tissue section. Using staining methods like H&E, these biomarkers may be difficult for humans to visually detect or quantify without the aid of additional testing. Using AI to infer these biomarkers from digital images of tissues may improve patient care, while also being faster and less expensive.

Computational pathology processes and devices disclosed herein may provide an integrated platform allowing a fully automated process including data ingestion, processing, and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to perform real-time monitoring and forecasting of health patterns at multiple geographic specificity levels.

The digital pathology images described above may be stored with tags and/or labels pertaining to the properties of the specimen or image of the digital pathology image, and such tags/labels may be incorrect or incomplete. Accordingly, systems, devices, and methods disclosed herein may identify and/or verify correct properties (e.g., pertaining to a specimen type) of a digital pathology image. Systems, devices, and methods disclosed herein may automatically predict the specimen or image properties of a digital pathology image without relying on the stored tags/labels. Further, systems, devices, and methods disclosed herein may quickly and correctly identify and/or verify a specimen type of a digital pathology image, or any information related to a digital pathology image, without necessarily accessing an LIS or analogous information database.

In one example, a system may be trained to identify various properties of a digital pathology image based on datasets of prior digital pathology images. The trained system may provide a classification for a specimen shown in a digital pathology image. The classification may help to provide treatment or diagnosis prediction(s) for a patient associated with the specimen.

Systems, devices, and methods disclosed herein may provide one or more examples of a specimen classification tool. An input to the tool may include a digital pathology image and any relevant additional inputs. Outputs of the tool may include global and/or local information about the specimen. A specimen may include a biopsy or surgical resection specimen.

Exemplary global outputs of the disclosed workflow(s) may contain information about an entire image, such as the specimen type, the overall quality of the cut of the specimen, the overall quality of the glass pathology slide itself, and/or tissue morphology characteristics. Exemplary local outputs may indicate information in specific regions of an image; for example, a particular image region may be classified as having blur or a crack in the slide. Systems, methods, and devices disclosed herein may use the disclosed specimen classification tool(s), as described in further detail below.

In addition, systems, methods, and devices disclosed herein may protect sensitive and legally protected information in the development and delivery of computational pathology services and products. Further, systems, methods, and devices disclosed herein may provide a security and privacy by design approach as well as production system protections for all data, including data belonging to a medical practice, patients, and/or customers.

Technical aspects disclosed herein may make digital pathology slides available to a vast community of pathologists and scientists, allowing a clinical site or institution to better control data sharing policies and ensure that data is securely stored and anonymized. As a result, the clinical site or institution may collaborate better with researchers around the world to develop AI solutions that benefit pathology and ultimately patients. If a user is part of a research group or university, technical aspects disclosed herein may allow for easier access to a clinical partner's data and leveraging existing infrastructure to build a custom algorithm using a software development kit (SDK).

A workflow using an integrated computing platform may offer (i) an AI-native digital pathology slides viewer, (ii) a suite of AI products, and/or (iii) a data ingestion appliance. The AI-native digital pathology slides viewer may comprise an interactive user interface or notification dashboard. The viewer may further support the collaboration and sharing of slide images. The suite of AI products may include products designed for different parts of the body (e.g., prostate), which may plug into different workflow steps and be user-customized for a specific diagnostic purpose or type of cancer. The data ingestion appliance to facilitate the transfer of digital pathology slides.

Figure 1:
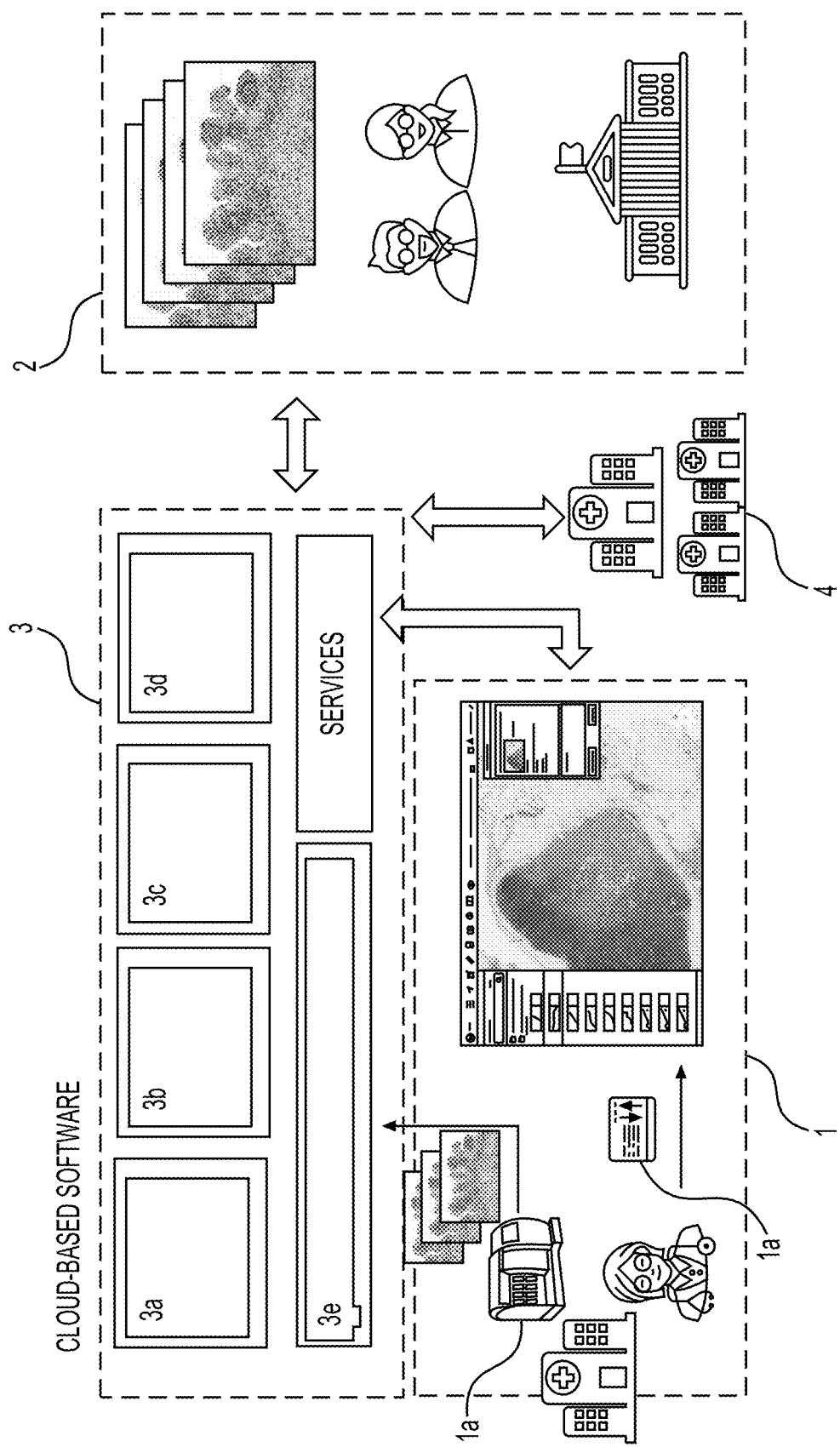
FIG. 1 is an exemplary global architecture of a platform for processing digital slides, according to an exemplary embodiment.

FIG. 1 depicts an exemplary schematic a hospital or clinical setting 1, an external group research institution or university 2, a cloud computing ecosystem 3, and another or secondary hospital or clinical setting 4. The hospital or clinical setting 1 may include an integrated scanner appliance and platform 1a. The platform 1a may be in communication with cloud computing ecosystem 3 (e.g., Amazon Web Services Cloud (AWS)). The cloud computing ecosystem 3 may be in communication with an external group research institution or university 2. In addition, cloud computing ecosystem 3 may be in communication with another hospital or clinical setting 4 outside of the originating hospital or clinical setting. Additionally, an external group research institution or university 2 may be in communication with the cloud computing ecosystem 3.

In an exemplary workflow, a pathologist with a dataset of whole slide images (WSIs) at the hospital location 1 may want to collaborate on a research project with scientists and researchers from the external research group or university 2. The group of researchers may need access to the pathologist's anonymized dataset to collaborate on the project. A scalable, reliable, and secure cloud storage 3e may enable controlled data sharing while remaining compliant and secure. Once this storage 3e is in place, the group of researchers may develop one or more AI modules or software development kits (SDKs) 3a, 3b, 3c, 3d customized to a specific research question or type of WSIs (e.g., for prostate cancer slides, etc.). Various AI solutions, in the form of the one or more AI modules or SDKs 3a, 3b, 3c, 3d, or other services, may be deployed in a same secure cloud computing ecosystem 3 as the cloud storage 3e. In addition, the one or more AI modules or SDKs 3a, 3b, 3c, 3d may be made available to and/or in communication with the platform 1a, the university 2, and/or the secondary hospital setting 4. Although one cloud storage 3e is shown, there may be a plurality of cloud storages 3e, each corresponding and/or dedicated to a single institution (e.g., external research group or university 2, or another external group, hospital, research university, etc.) to prevent leakage between institutions and/or customers.

The pathologist at the hospital location 1 may leverage appropriate tools to view results and images of the one or more third party AI modules 3a, 3b, 3c, 3d. The researchers at the university 2 may gather valuable feedback and/or use other services from the cloud computing ecosystem 3. Together, collaborators may decide whether to make the one or more third party AI modules 3a, 3b, 3c, 3d available to other institutions and locations (e.g., secondary hospital 4) and incorporate various other information and data into the workflow, all while maintaining security and privacy. The collaborators may further decide to update their one or more AI modules 3a, 3b, 3c, and 3d and make those updates available in the cloud computing ecosystem 3. Different users, such as a pathologist at hospital location 1, researches at university 2, and/or others with access may select, retrieve, and/or download from among multiple AI modules or SDKs 3a, 3b, 3c, and 3d developed by different users (e.g., different universities or other third parties), and these AI modules or SDKs 3a, 3b, 3c, and 3d may be easily swapped out with others and/or updated.

The one or more AI modules or SDKs 3a, 3b, 3c, 3d may be simple, usable and technically sound. The one or more AI modules or SDKs 3a, 3b, 3c, 3d may require less effort to customize for specific use cases, may be self-contained, may be able to run locally, and may reduce or minimize exposed code. The one or more AI modules or SDKs 3a, 3b, 3c, 3d may be easy to learn, easy to integrate in a developer's workflow, be well-documented but able to be used without documentation, provide examples, and require low support. The one or more AI modules or SDKs 3a, 3b, 3c, 3d may be stable, thoroughly tested, secure, backwards compatible, well-packaged, and versioned. The one or more AI modules or SDKs 3a, 3b, 3c, 3d may be plugged into platform architecture in a number of places, as desired by a user (e.g., a pathologist, a researcher, etc.) and dependent on a desired function of the one or more AI modules or SDKs 3a, 3b, 3c, 3d.

The platform 1a and workflows disclosed herein may enhance collaboration between users. Collaboration may be between a user of the platform 1a in an institution (e.g., hospital 1) to a user in the same institution, a user of another institution (with access to the platform 1a, a person of another institution (e.g., secondary hospital 4) without access to the platform 1a, or an external individual (e.g., at external institution 2). Users of the platform 1a may be able to simultaneously open and view same slides and cases. Users may additionally send links of cases and slides, where the cases and slides may be identified, deidentified, anonymized, or may publically or privately comment and annotate. In a conference or a conference-like setting, groups may review the same cases and slides with a lead user navigating the slide and where the rest of the group may be able to see the slide on a personal screen (similar to a multi-headed microscope). In other settings, links of cases and slides may be received and/or downloaded based on institutional download limits (e.g., students at universities). AI results may be included in sharing options.

Figure 2:
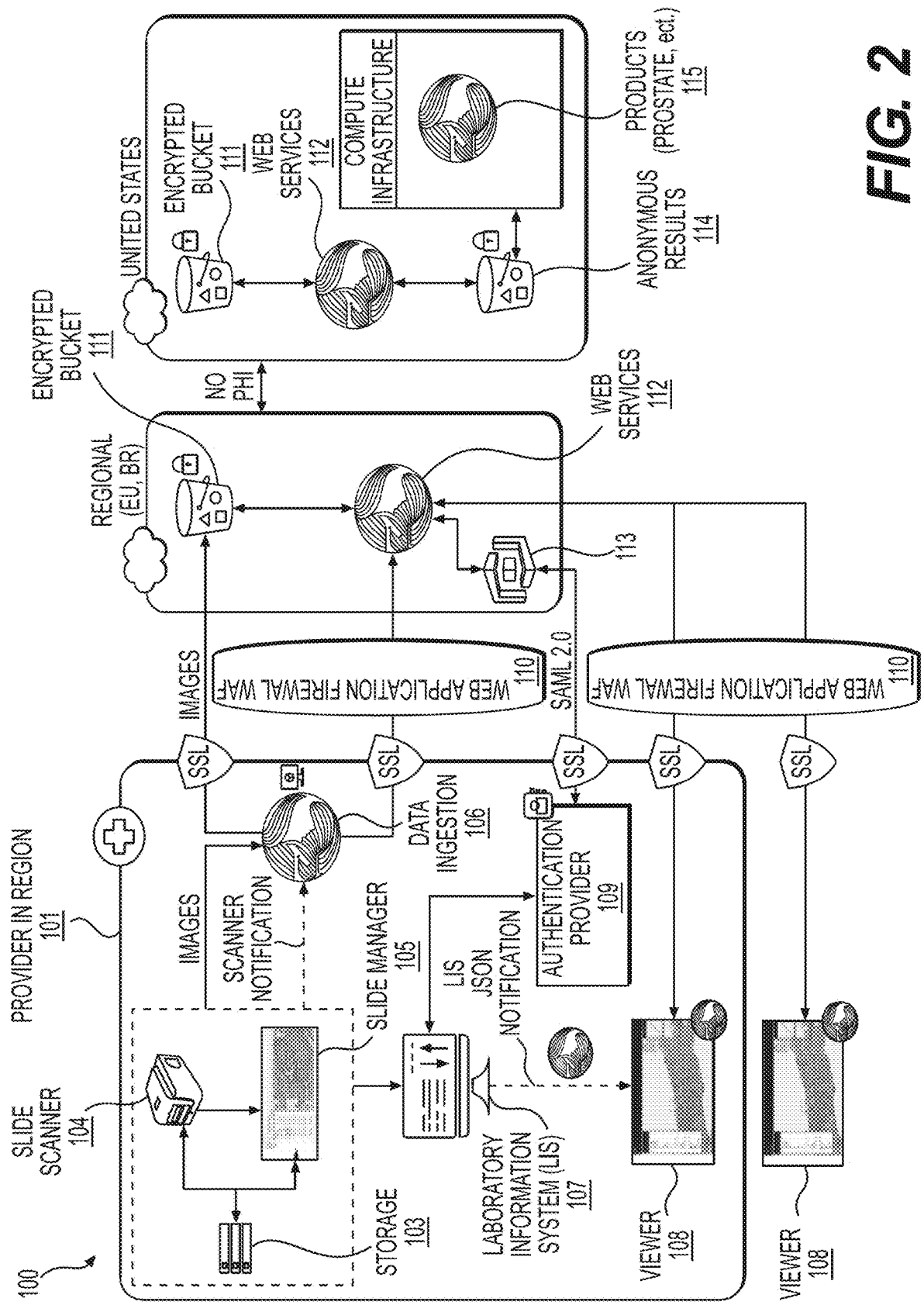
FIG. 2 is a workflow illustrating an exemplary method for use of the platform with an artificial intelligence (AI) output, according to an exemplary embodiment.

FIG. 2 depicts an exemplary global architecture 100 of a platform for processing digital slides. This architecture may be used with the one or more SDKs or third party AI modules 3a, 3b, 3c, 3d as discussed above with FIG. 1. One or more embodiments may use a cloud provider such as an Infrastructure-as-a-Service (IaaS) and Platform-as-a-Service (PaaS) provider to provide a scalable, reliable, secure, available service to customers on a global scale. The exemplary global architecture 100 may include use by a provider in a region 101, and may send digital slides and images to other regions, such as in the European Union or the United States. A region may refer to locations having different sizes and characteristics. For example, a region may correspond to a country, a city, and/or a hospital, etc. Any metadata related to patients may also be encrypted and stored in that region. The global architecture 100 may be developed to account for compliance, reliability, security and privacy across any region. The global architecture 100 may be configured such that there may be no default region where metadata is stored (for example, such that metadata is not automatically stored in a specific region 101, such as the U.S., unless authorized, such as when the patient lives in the specific region 101).

Within the provider in region or location 101, the global architecture 100 may include a Whole Slide Image (WSI) system 102, where WSIs are digitized and may be stored locally in a storage 103. WSIs may be scanned by slide scanner 104, and sent from the slide scanner 104 to the slide manager 105. From the WSI system 102, digitized images may be sent to either a data ingestion appliance 106 or a Laboratory Information System (LIS) 107. If the images are sent to LIS 107, a user may be notified by a JavaScript Object Notation (JSON) notification that images are available to be viewed on viewer 108. The viewer 108 may a web-based software product that facilitates viewing and navigating of digitized pathology slides that would otherwise be appropriate for manual visualization by conventional light microscopy. The viewer 108 may be configured for in vitro diagnostic use.

If the images are instead sent to data ingestion appliance 106, images may be further sent through Web Application Firewall (WAF) 110 to web services 112, located outside of the originating region 101 of the slides. From web services 112, images may be sent to a web service console 113 and then back to the original region 101 for additional processing, review, or authentication by authentication provider 109. Images may also be sent through WAF 110 to a viewer 108 outside of the provider in region 101.

Alternatively, images may be sent from the data ingestion appliance 106 to a unique encrypted S3 bucket 111. The encrypted S3 bucket 111 may be physically located in a number of different regions or privacy jurisdictions, for example in the European Union (EU) (such as in London or Frankfurt), Brazil (such as in Sao Paulo), or in the US (such as in Northern Virginia). As described above, a region may be refer to locations having different sizes and characteristics. A privacy jurisdiction may refer to an area that follows the same or similar privacy laws or policies (e.g., EU or US). Regions may be areas or locations that are authorized to access the same information (e.g., a hospital). No Protected Health Information (PHI) associated with any of the images or slides may be permitted to travel between encrypted S3 buckets 111 that are located in different regions. If the encrypted S3 bucket 111 is located within the US, images may be sent to and from web services 112, which may further send images to another encrypted S3 bucket 114 for holding anonymous results. These anonymized results may be used in other products 115, including diagnostic tools aimed at a specific area of the body such as the prostate, etc.

Images (e.g., whole slide images or WSIs) may be automatically scanned by WSIs scanners 104 and automatically and securely ingested and deposited by WSI scanners 104 into local storage 103. These images may be automatically copied into secure cloud storage (e.g., a fully automated process). Once the images are received, the global architecture 100 may leverage the latest advances in cloud computing to automatically perform AI computations at scale. The global architecture 100 may provide a state-of-the-art experience in viewing the uploaded images and predictions generated by AI products.

The global architecture 100 may maintain strict enforcement of regulatory requirements for PHI, including preventing patient information from leaving its originating geography. The global architecture 100 and/or product architecture may be developed to account for compliance, reliability, security and privacy such that PHI is held in the originating region. The global architecture 100 may be configured such that uploaded images and/or metadata may be stored in storage dedicated to a specific institution.

As illustrated in FIG. 2, identifiable patient information may be kept in the region where the practice is located. All scanned images may be kept in an encrypted S3 bucket 111 physically located in any of the regions. Pathology data from different institutions may be separated from each other by storing the data from different institutions in different buckets.

The global architecture 100 may provide well-defined application programming interface (API) endpoints for data ingestion. To reduce or minimize the exposure of sensitive data, a specific endpoint (e.g., regional API endpoint) and a unique S3 bucket 111 may be provided to limit a number of firewall rules to be created. This endpoint may be stable to reduce a risk of service disruption.

The global architecture 100 may leverage authentication provider(s). The global architecture 100 may integrate with an authentication provider using a protocol (e.g., Security Assertion Markup Language (SAML) 2.0 protocol) allowing an information technology (IT) department to manage credentials and access for authorized accounts.

The global architecture 100 may provide or enable customer segregation. Uploaded images may be stored in cloud storage dedicated to an institution to prevent data leakages between customers. Other data may be multi-tenant and not necessarily segmented from other customer's data. The global architecture 100 may perform a backup of customer data on a periodic basis and keep records for a predetermined time period (e.g., six years) in order to provide disaster recovery capabilities. The predetermined time period may be based on contractual agreements, rules, policies, etc.

Customers may remain the owners of their data. Customers' data may be used to improve products and to further develop the platform and related products and services.

A cohesive Data Loss Prevention (DLP) solution may be deployed to detect any potential data breaches or leakages, monitor data flows and protect sensitive information (e.g., customer data and intellectual property). The security standards may align with selected standards (e.g., HIPAA<ISO 27001, GDPR and HITRUST).

The global architecture 100 may include a key card management system, and access to physical offices may be controlled by the key card management system. Key card access may also control entry to restricted office areas. The logs of the key card system may be maintained in a secure log management tool that is used for monitoring, alerting, and event correlation. Physical offices also have video monitoring at all physical entryways.

The global architecture 100 may include a Version Control System requiring employee authentication and enabling auditability, and Source code may be stored securely in the Version Control System. Code changes may be peer-reviewed for quality and potential security issues. Further, component and product versioning may enable full traceability.

In addition to traditional testing and/or testing for correctness, regression, stability, and validity, the global architecture 100 may perform or enable performance of Static Application Security Testing (SAST) and Dynamic Application Security Testing (DAST) for all the components forming the final products. For maximum efficiency, these tools may be integrated within a software development life cycle (SDLC) and within a continuous integration platform. Throughout an entire SDLC, from ideation to delivery, standard industry practices may be used. Source code, etc. may be stored securely in a Version Control System requiring employee authentication and enabling auditability. All code changes may be peer-reviewed for quality and potential security issues. The global architecture may enable full traceability.

The global architecture 100 may include patch management and maintain a regular patching procedure and schedule. The global architecture 100 may conduct operating system patching monthly for all management systems. The global architecture 100 may manage product and third-party software patching throughout the development of the product and deployed with each release. The global architecture 100 and/or processes disclosed herein may comprise a Quality Management System. The Quality Management System may be maintained in conformance with applicable standards (e.g., ISO 13485:2016) and regulations. The Quality Management System may monitor and/or analyze processes that are executed in connection with the global architecture 100, interactions of these processes, risk of these processes to the Quality Management System and product quality as assessed with a risk approach (e.g., meeting ISO 14971 standard), resource allocation to support and monitor these processes, effectiveness of measurement and analytical activities associated with processes, and mechanisms associated with continual improvement of processes.

The global architecture 100 may include vulnerability management. The global architecture 100 may use security tools to conduct active security and vulnerability scans of the product and production environment. The global architecture 100 may log identified issues and perform a risk assessment. A security team may conduct regular assessments, reviews, and audits of the environment. Further, the team may track and remediate vulnerability issues.

The global architecture 100 may include malware prevention, which may include the use of antivirus and malware detection tools. The global architecture 100 may include a firewall to control and monitor network traffic.

Figure 3A:
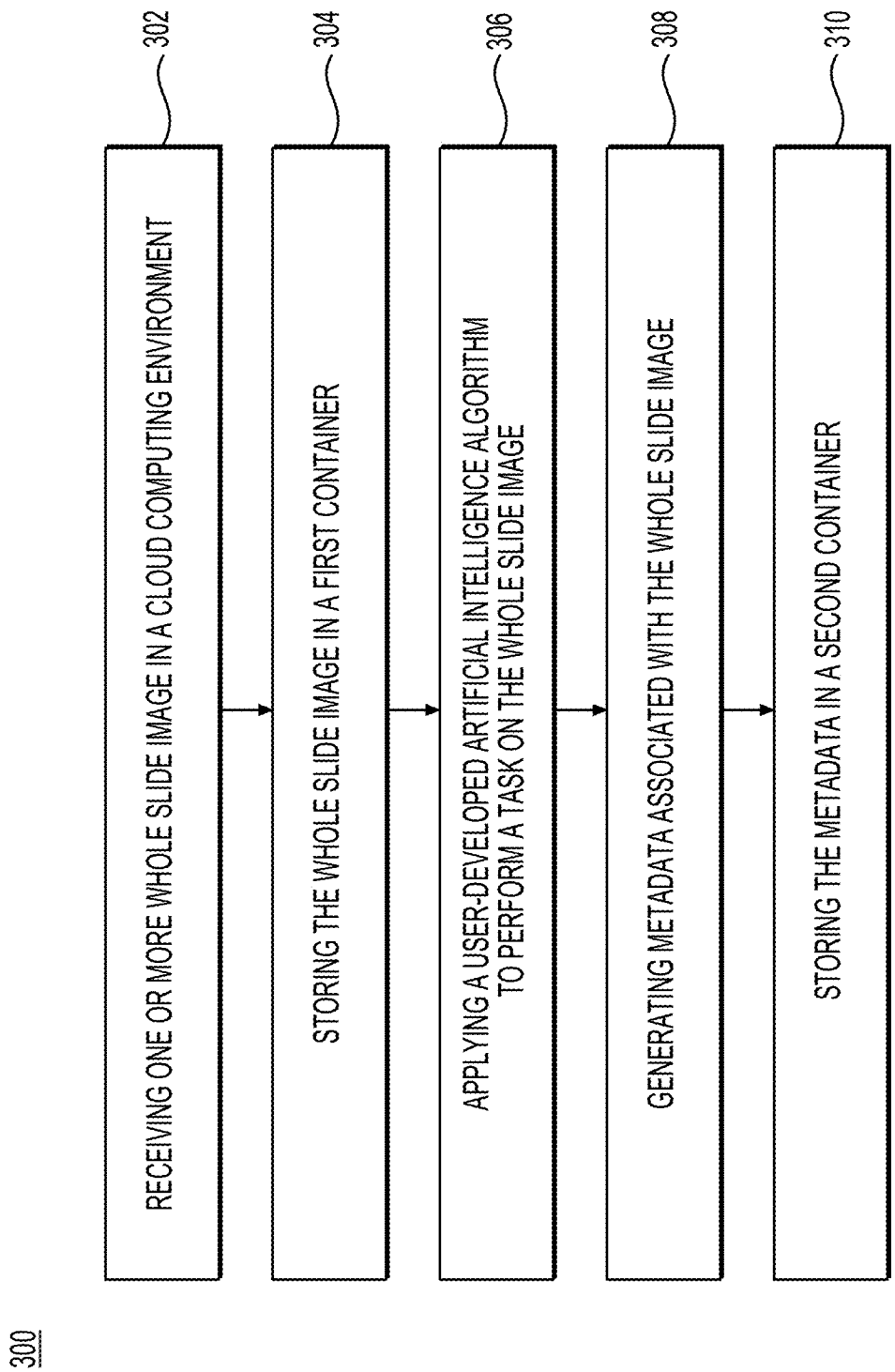
FIGS. 3A-3B is a flowchart illustrating an exemplary method for use of the platform, according to an exemplary embodiment.
Figure 3B:
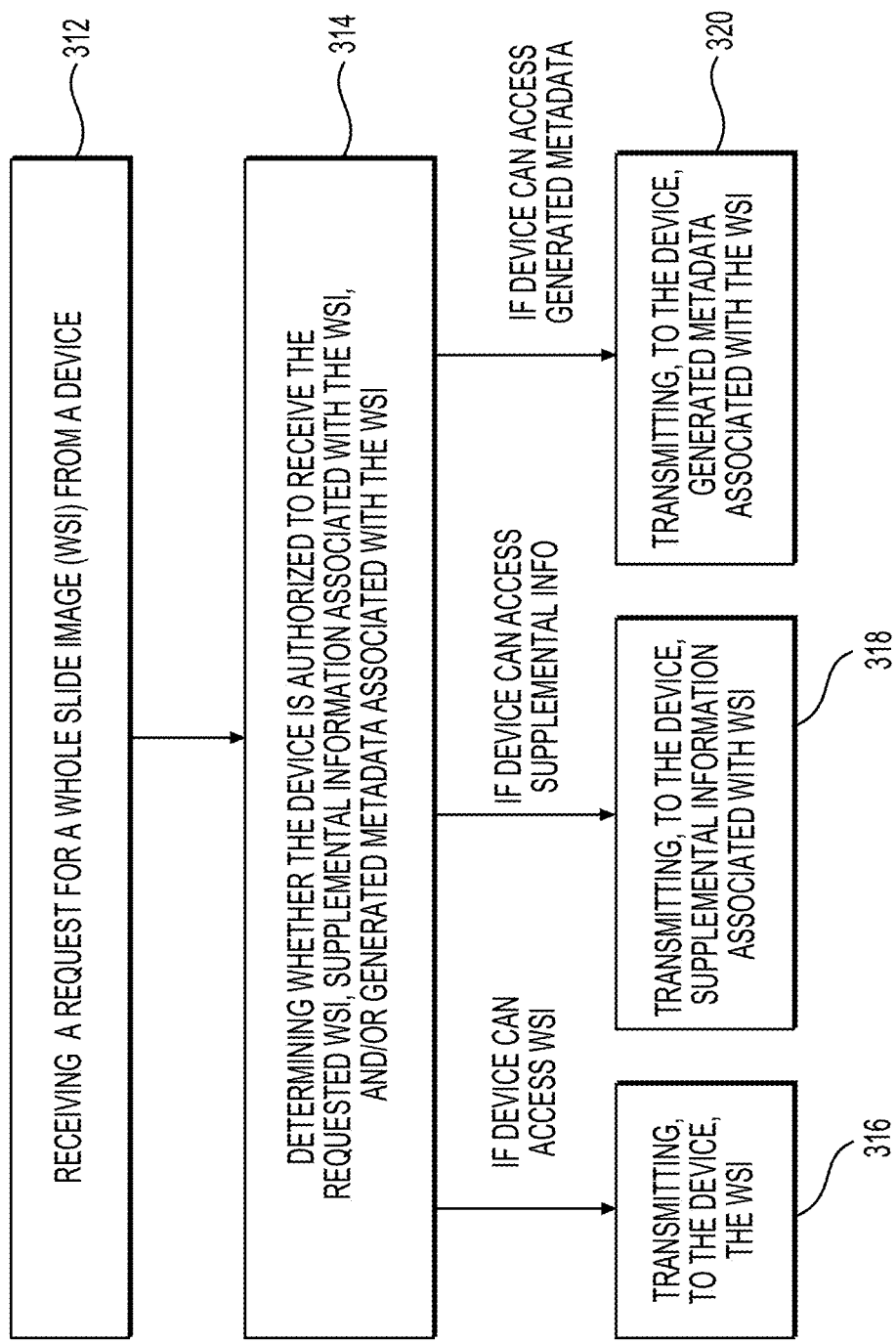

FIGS. 3A and 3B are workflows illustrating an exemplary method for use of a platform with an AI algorithm, according to an exemplary embodiment. For example, AI may be applied in many aspects of a complete workflow used by the platform, either automatically or in response to a request by a user. FIG. 3A illustrates a portion of the workflow to generate metadata, described as method 300, and FIG. 3B illustrates a portion of the workflow to send WSIs, supplemental information associated with the WSI, and/or generated metadata from the WSI from FIG. 3A, which is described as method 350. In some examples, methods 300 and 350 can be combined into a single method.

Referring to FIG. 3A, an exemplary method 300 for using a platform (e.g., platform 1a of FIG. 1) with an AI output may include one or more of the following steps. In step 302, the method 300 may include receiving one or more whole slide images (WSIs) in a cloud computing environment (e.g., cloud computing ecosystem 3 of FIG. 1) from a first user in a first location or region (e.g., hospital 1 in FIG. 1) and/or from a first user associated with a first patient in the first location and/or region. The WSI may depict a medical sample associated with a patient. The slides may be scanned in by the slide scanner 104 and stored in WSI system 102, as described above in FIG. 2. Step 302 of receiving the one or more WSIs may also include receiving additional or supplemental information associated with the WSI, the medical sample, and/or the patient.

In step 304, the method 300 may include storing the whole slide image in a first container in the first region. The container may be any data storage service such as a simple storage service encrypted bucket (e.g., encrypted S3 bucket 111 in FIG. 2). Storing the received whole slide image may include performing automatic AI-based ingestion of the received whole slide image.

In step 306, the method 300 may include applying a user-developed or customized artificial intelligence (AI) model or algorithm (e.g., third party AI module 3a, 3b, 3c, 3d of FIG. 1) to perform a task on the one or more WSI. The task may comprise at least one step to determine a characteristic of the medical sample in the WSI. The AI may incorporate not only the slide itself, but also associated patient data, such as a genetic profile, patient history, other related slides, radiology data, molecular data, clinical data, etc. that is received.

The user-developed AI model or algorithm may have been developed by and received from the first user and/or a second user in a second location or region (e.g., researchers at institution 2 in FIG. 1). Thus, the method 300 may include a step of receiving the user-developed AI model or algorithm into the cloud computing environment (e.g., cloud computing ecosystem 3 of FIG. 1). The user-developed AI model or algorithm may be among a plurality of user-developed AI models or algorithms stored in the cloud computing environment. Each of the plurality of AI models or algorithm may have been developed by different users (e.g., third, fourth, etc. users) in different locations and/or regions (e.g., third, fourth, etc. regions), such as hospital 1, institution 2, additional hospital 4, or another institution, organization, or hospital external to hospital 1.

In developing the user-developed AI model or algorithm, the second user may have received anonymized slides or associated data (e.g., metadata associated with a slide) from the first user. The step 302 of receiving one or more whole slide images may include receiving one or more anonymized whole slide images, and/or the method 300 may include a step of anonymizing the slides or associated data and/or a step of sending anonymized slides or associated data to the second user.

The step 306 of applying the user-developed AI model or algorithm may include selecting one or more user-developed AI models or algorithms among the plurality of user-developed AI models or algorithms stored in the cloud computing environment. This selection may be based on a type of request received (e.g., metadata or information desired), a command for a particular user-developed AI model(s), additional or supplemental information or metadata already associated with the WSI and/or additionally received before step 306, rules or policies received by the first user, and/or rules or policies received by the second user and/or users who submitted the user-developed AI modes to the cloud computing environment (for example, certain users or institutions may wish to bar other users or institutions from using their AI models based on licensing agreements, etc.). For example, the method 300 may include a step of receiving a request to analyze a whole slide image and/or a request to apply a user-developed AI model or algorithm to a whole slide image.

In step 308, the method 300 may include, based on the determined characteristic of the one or more WSI, generating metadata associated with the WSI. The metadata output may be generated from the slide. The metadata may be generated according to a received request and/or a selected user-developed AI model or algorithm.

The metadata output may be customizable according to user (e.g., requester) wishes or preferences, and may include, but is not limited to, (i) case assignment, (ii) case worklist, (iii) case preparation, (iv) slide tray, (v) slide viewer, and/or (vi) pathology report. With case assignment metadata, cases may be assigned to an expert pathologist based on the AI output to inform pathologists automatically about the case and/or to assign cases to multiple pathologists. With case worklist metadata, cases may be sent to a worklist to organize or prioritize cases according to urgency, to visualize cases according to importance, and/or to search cases by a desired outcome.

With case preparation metadata, cases may be prepared to order special stains needed for a patient, to suggest clinical trials for the patient, and/or to trigger a rescan of a slide, e.g., based on poor slide quality. With slide tray metadata, slides may be organized within a case according to urgency or severity, to visualize slides according to importance, and/or to search cases by detected outcome. With slide viewer metadata, a slide may be viewed with an overlay of a graphical AI result, to summarize an AI result textually, and/or to suggest or to trigger follow-up studies. With pathology report metadata, a pathology report may be pre-filled with the AI results of the workflow.

The metadata may be output as a heatmap, as described in more detail with reference to FIG. 7. The heatmap may comprise a graphical prediction of a likelihood of an attribute in the medical specimen. The AI and/or metadata output may additionally depend on what user-developed AI model or algorithm (e.g., AI module or SDK 3a, 3b, 3c, and/or 3d of FIG. 1) is used in conjunction with the platform.

In step 310, the method 300 may include storing the metadata in a second container. The second container may be different from the first container. The second container may be any data storage service such as a simple storage encrypted bucket (e.g., additional encrypted S3 bucket 111 of FIG. 2) in a location or region that is the same as the first location or region, or alternatively that is different from the first location or region, such as the second location or region and/or a third location or region. In some examples, the user-developed AI models or algorithms may be modified and/or refined based on the generated metadata and/or any additional information (e.g., long-term results) received into the cloud computing environment (e.g., in cloud ecosystem 3 and/or storage 3e of FIG. 1), and accuracy and efficiency of the user-developed AI models or algorithms may be improved. In some examples, each institution, location, region, etc. may have its own container or bucket for generated metadata.

Referring to FIG. 3B, method 350 may include a step 312 of receiving a request for one or more whole slide images from a device (e.g., a computer or other mobile device, an image system at a hospital, etc.) The method 350 may include a step 314 of determining, based on a physical location of the device, whether the device is authorized to receive or access the whole slide image, supplemental information associated with the whole slide image, and/or generated metadata associated with the whole slide image. Step 314 may include, for example, determining whether the device is located in a same or a different location (e.g., hospital), region (e.g., city or local hospital system), and/or privacy jurisdiction (e.g., US) of the first container, the second container, the first user (i.e., the sender of the initial whole slide image to the cloud computing environment), and/or the patient. Step 314 may include determining whether the device and/or user is authorized to access information in the first container and/or the second container.

Step 314 may also determine whether the device is authorized based on an identity and/or credentials of the requester or device and/or based on any policies, permissions, or rules. Policies, permissions, or rules may be associated with or received from (i) the first user (e.g., hospital 1 in FIG. 1), (ii) the second user who created the user-developed AI model or algorithm used to generate the metadata, (iii) the second container, and/or (iii) external rules, regulations, laws, or policies within a privacy jurisdiction (e.g., GDPR where the patient, hospital, and/or the first or second containers are located within the EU). The method 350 may include a step of receiving, storing, and/or determining the above-described policies, permissions, or rules. Alternatively or in addition thereto, step 314 may include determining whether the whole slide image, supplemental information, and/or generated metadata should be modified based on any of the above factors used to determine authorization.

The method 350 may include, in step 316, transmitting or outputting, to the device, the requested whole slide image if, in step 314, it was determined that the device was authorized to access the whole slide image. As an example, the WSI may be transmitted from the first container. Alternatively or in addition thereto, step 316 may include modifying the whole slide image and/or generating a new whole slide image based on any modifications determined in step 314.

The method 350 may include, in step 318, transmitting or outputting, to the device, any supplemental information associated with the WSI if, in step 314, it was determined that the device was authorized to access any such supplemental information. Step 314 may include determining portions or types of supplemental information authorized and not authorized, and step 318 may include transmitting only those portions or types of supplemental information that are authorized. The supplemental information may be transmitted from the first container and/or storage. Alternatively or in addition thereto, step 318 may include modifying the supplemental information and/or generating new supplemental information based on any modifications determined in step 314.

The method 350 may include, in step 320, transmitting or outputting, to the device, the generated metadata associated with the WSI if, in step 314, it was determined that the device was authorized to access the generated metadata. Like with step 316, step 314 may include determining portions or types of the generated metadata authorized and not authorized, and step 320 may include transmitting only those portions or types of generated metadata that are authorized. The generated metadata may be transmitted from the second container. Alternatively or in addition thereto, step 320 may include modifying the generated metadata and/or generating new metadata based on any modifications determined in step 314.

Any one or all of 316, 318, and 320 may be performed based on the determinations made in step 314. For example, the device is from a same hospital or physician from which the WSI was received in step 302, then step 314 may determine that the hospital is allowed to access the WSI and all information (both supplemental and generated metadata) associated with the WSI, and all of steps 316, 318, and 320 may be performed. If the device is from a researcher, there may be policies in place based on collaboration agreements, joint development agreements, laws, etc. between the researcher and a hospital allowing the researcher to access certain WSIs submitted by the hospital (e.g., those pertaining to cancer) and certain supplemental data or generated metadata, but not other information (e.g., identifying information), and so step 314 may determine that the researcher is allowed to access the WSIs and some or all of the supplemental information and/or generated metadata, and step 316 may be performed, along with steps 318 and 320 accordingly.

In another example, the device may be, as determined during step 314, from an unrecognized or unauthorized location, region, or user, and none of steps 316, 318, 320 may be performed. In yet another example, some devices, based on user identity, may be determined in step 314 as being authorized to access generated metadata but not the WSIs and/or supplemental data, and step 316 may not be performed, but steps 318 and 320 may be performed accordingly.

FIGS. 4A-4C are exemplary architectures of a data ingestion appliance and the integration of the data ingestion appliance to the platform architecture, according to exemplary embodiments. An exemplary architecture of a data ingestion appliance may provide a Data Ingestion Appliance able to receive notifications when slides are digitized as images, and then may queue and upload the new images. Once ready, the acquired images may be encrypted (e.g., using TLS 1.2+) and sent to secure cloud storage where they will be processed.

The Data Ingestion Appliance may seamlessly integrate with one or more scanners, such as slide scanner 104. Data in transit may be encrypted (e.g., using TLS 1.2+ with AES-256 encryption, via industry standard HTTPS). The Data Ingestion Appliance may be distributed as an Open Virtual Appliance (OVA) file.

Referring to FIG. 4A, data ingestion may comprise a WSI system 102, a laboratory information system (LIS) 107, and a bridge 120. The WSI system 102 may further comprise an image management system (IMS) or slide manager 105, a storage 103, and a slide scanner 104, where all components are able to communicate and send slide images between one another.

Here, an integration between the LIS 107 and the slide manager 105 may be established or pre-existing. This interface may allow digitized slides to be accessible from the LIS 107. A bridge 120 may be deployed and configured to consume all information from the interface built from the scanner 104, such as the WSI system 102. The interface may be built in Health Level 7 (HL7), Fast Healthcare Interoperability Resources (FHIR), databases, Representational state transfer (REST) application programming interfaces (API), etc.

The bridge 120 may be designed as a standalone product or module that is easily installed on-premise as a virtual appliance, local to the scanner(s) 104. The bridge 120 may upload slides as they are digitized. Once ready, the acquired images and associated metadata may be sent to secure cloud storage 3e to be processed. The bridge 120 may be built to seamlessly integrate with all digital slide scanners 104 with automation enabled. All data in transit may be encrypted using TLS 1.2+ with AES-256 encryption, via industry standard HTTPS. The bridge 120 may be distributed as an Open Virtual Appliance (OVA) file.

Any supplemental information may be obtained from the LIS 107. From the bridge 120, images and associated information may be sent to a cloud 121. This example allows bridge 120 to be notified of newly digitized images and pull associated data from a combination of the scanner 104 and/or slide manager 105 and LIS 107.

Referring to FIG. 4B, there may be no integration between any part of the WSI system 102 and the LIS 107. In this option, the WSI system 102 does not contain a slide manager 105. Here, the bridge 120 may be deployed and configured as a main system to consume digitized images from the scanner 104 and the output storage 103. The bridge 120 may also be used to retrieve patient and case metadata from the LIS 107. The bridge 120 may then send any of this information about the digitized images to the LIS 107 or may send images and associated information to the cloud 121. This example allows bridge 120 to be notified of newly digitized images upon and create a bi-directional integration with LIS 107 to reconcile the scanned images and information stored in the LIS 107.

Referring to FIG. 4C, here, an integration may be established or pre-existing between the LIS 107 and the slide manager 105 of WSI system 102 to allow digitized slides to be accessible from the LIS 107. Through this interface, patient, case and slide information may be available. The bridge 120 may be deployed and configured to consume all information from the interface built against the scanner 104 system. From the bridge 120, images and associated information may be sent to cloud 121. With a pre-existing integration between the LIS 107 and the slide management system 105 and/or scanner 104, mechanisms to pull images and associated metadata from the slide management system 105 and/or scanner 104 may be developed.

FIGS. 5A-C are exemplary architectures of a laboratory information system (LIS) and the integration of the LIS to the platform architecture or other hospital systems, according to exemplary embodiments.

Referring to FIG. 5A, the LIS 107 may communicate one-way with a viewer 108. Once the viewer 108 is opened, either automatically or in response to a request from a user, a protocol such as HTTPs may request passing all information to identify a case and a patient. This information may be sent for verification by the LIS 107 to web product 115. The information may be authenticated to a hospital's authentication provider 109 using SAML or another standard for exchanging authentication. Once authenticated, the images and any associated AI results may be streamed or displayed on the viewer 108. This example may allow a direct link to cases or images to be incorporated into LIS 107, allowing for viewer 108 to be opened as part of an existing workflow.

Referring to FIG. 5B, the LIS 107 may communicate directly with viewer 108. The web product 115 may also communicate directly with LIS 107, establishing bi-directional integration of the LIS 107. Once the viewer 108 is opened, either automatically or in response to a request from a user, a protocol such as HTTPs may request passing all information to identify a case and a patient. This information may be sent for verification by the LIS 107 to web product 115. The information may be authenticated to a hospital's authentication provider 109 using SAML or another standard for exchanging authentication. Once authenticated, the images and any associated AI results may be streamed or displayed on the viewer 108. This example may allow a set of APIs (e.g., REST APIs) that can be used to pull data out of the platform (e.g. status, etc.) and allow for information to propagate to the LIS 107 or any other existing health system. The LIS 107 may pull information from the web product 115-provided REST APIs.

Referring to FIG. 5C, the LIS 107 may communicate directly with viewer 108. The web product 115 may also communicate with LIS 107 via the bridge 120, establishing bi-directional integration of the LIS 107. Once the viewer 108 is opened, either automatically or in response to a request from a user, a protocol such as HTTPs may request passing all information to identify a case and a patient. This information may be sent for verification by the LIS 107 to web product 115. The information may be authenticated to a hospital's authentication provider 109 using SAML or another standard for exchanging authentication. Once authenticated, the images and any associated AI results may be streamed or displayed on the viewer 108. Additionally, the bridge 120 may be used for more sophisticated writing operations to the LIS 107 or other systems, such as electronic medical records (EMR) or hospital system 130, over any protocol. This example may allow bridge 120 to be used to pull data out of the platform and allow information to propagate to the LIS 107 or any other existing health system.

FIG. 6 is an exemplary architecture of a slide viewer, according to an exemplary embodiment of the present disclosure. The viewer may be used for in vitro diagnostic use as an aid to the pathologist to review and interpret digitized images of a pathology specimen or case, which may include protected health information (PHI) about an associated patient. For example, a viewer may comprise an AI-native web-based software product that facilitates improved viewing and navigating of digitized pathology images of slides. The exemplary architecture may allow a user (e.g., pathologist) to view digitized slide images or diagnostic cases.

The exemplary architecture 600 may include a number of components in a local setting as well as a number of components based in a cloud computing service, such as cloud 140. Within the local setting, there may be products such as a web application 131, a worklist 132, and a manager product 133 with a corresponding user, e.g., a pathologist, administrator, etc. Any one of web application 131, worklist 132, and/or manager product 133 may send slides or other information through slide subscriber 137 to slide queue 136. Additionally, there may be a slide scanner 104, a file system 134, and a database 138 at an institution A with virtual machine 171. The virtual machine may include a watcher 135 that may retrieve slides from file system 134 or database 138 before sending slides to a slide queue 136.

In the cloud 140, all images may be required to be screened through a WAF 110. Then, slides may be sent to a cloud-based worklist application 132, an internal application load balancer (ALB) 146 or external ALB 147, or to a web framework 172.

If the images are sent to internal ALB 146, the internal ALB 146 may then send images to an institution API 148. In turn, the institution API 148 may send images to a SQL instance 149, where they may be stored. The institution API 148 may also send the images to a case subscriber 152. If requested, either automatically or in response to a request from a user, the case API 152 will send images to a cluster region 153, which may comprise a main database 154 and a regional database 155.

If the images are sent to external ALB 147, they may then be sent on to a data ingestion appliance 106 and/or to a regional topic 174. From the regional topic 174, images may be sent to a case queue 150 and then a case subscriber 151, or to case API 152. As described above, case API 152 may send images to a cluster region 153, which comprises a main database 154 and a regional database 155. Alternatively, images may be sent from the external ALB 147 directly to the case 152, or to instance manager 149. Further, the external ALB 147 may send images directly to case queue 150.

External ALB may also send images to worklist 132 or to server 141. Server 141 may comprise web application viewer 142 and file system 143. File system 143 may store slide images on the server 141. The server 141 may send images on to web service console 113 after a user is authenticated, which in turn may send images from the cloud 140 to the active directory 170.

From the web application viewer 142, images may also be sent to cache 144, which stores project and user information along with application logs, or to one of two buckets. One bucket may be the inference result bucket 145, and the other may be a bucket 111 associated with institution A 101. Alternatively, the web application viewer may send images back to an internal ALB 146.

As illustrated in FIGS. 7A and 7B, one or more embodiments may provide an architecture for computational pathology processes and devices (e.g., prostate cancer detection). The architecture may be used to apply AI and machine learning models to images from slides which include specimens taken from part(s) of the body, and generate additional metadata (e.g., heatmap) related to the AI and machine learning models. A heatmap may be only one possible return value of the computational pathology processes and devices. While a heatmap is described in detail below, other return values may include an overlay image, text, or other information.

A heatmap may be a two-dimensional (2D) image that identifies a probability of cancer for each area of the image from the slide. For example, each pixel of the image may be assigned a value between 0 and 1, with a higher number corresponding to a higher probability of cancer in that particular area of the image.

Referring to FIG. 7A, architecture 700 of the disclosed computational pathology processes and devices may be based in a cloud services provider 140. The processes may begin with a response to a trigger 160, which may send a message to a prediction module 161. The prediction module 161 may send a prediction to a viewer heatmap 164, which may use the prediction to create an additional heatmap 165 or heatmap 166. Heatmap 166 may be zipped and sent to a results bucket 168, and may additionally fetch a heatmap from the results bucket 168.

Prediction module 161 may also send an uploaded slide to a prediction classification module 162. The prediction classification module 162 may either send the slide to an additional classification queue 163 or to a prediction classification 167. From the prediction classification 167, an uploaded heatmap may be sent to results bucket 168. Alternatively, the prediction classification 167 may fetch a prostate slide from slide bucket 169.

Referring to FIG. 7B, a method 710 may include a step 702 of receiving, in response to a trigger (e.g., trigger 160 in FIG. 7A, such as files being uploaded or scanned, a user input, etc.), one or more messages. For example, the one or more messages may be received into a notification service to be enqueued. The method 710 may include a step 704 of processing, sending, and/or forwarding the one or more messages. For example, step 704 may include processing the one or more messages, sending the one or more messages to a classification queue, and forwarding the one or more messages to a classification worker service. If an error occurs and a message is unable to be processed, the message may be sent to a dead letter queue to be later analyzed.

The method may include, in step 706, applying a trained machine learning model to a slide or whole slide image and/or performing a computation using a trained machine learning model to identify one or more biomarkers of interest from a relevant tissue and to exclude an irrelevant tissue from analysis. For every message received at the classification worker service, the slide or WSIs (e.g., prostate slides) may be retrieved and a computation may be performed. The computation may be performed using a machine learning model that is trained to identify the biomarker(s) of interest from relevant tissue (e.g., cancer tissue), with irrelevant tissue excluded from analysis.

The method 710 may include, in step 708, creating or determining a return value. The return value may include a heatmap (e.g., prostate heatmap) that shows a likelihood of a disease (e.g., cancer) in any part of the image. The method 710 may include, in step 712, outputting or uploading the return value (e.g., as a heatmap) to an electronic storage device (e.g., storage 3e in FIG. 1 in cloud computing environment or cloud computing ecosystem 3 in FIG. 1). Further, after the computation, the classification worker service may push a notification back to the notification service indicating whether the return value (e.g., heatmap) was prepared or whether the process failed. The method 710 may be performed behind a WAF (e.g., WAF 110 in FIG. 2). The method 710 may be separated from one or more administrative and/or development resources. The method 710 may further comprise prohibiting a collection of customer data from leaving a location where performing the computation, creating the return value, outputting the return value, or where other steps of the method 710 take place.

Further, the notification service may, based on the notification received from the classification worker service, send a message to a viewer return value queue (e.g., viewer heatmap queue). The messages may then be processed sequentially or in parallel by the return value queue and forwarded to a return value worker service (e.g., heatmap worker service). If an error occurs and a message is unable to processed, the message may be sent to a dead letter queue to be later analyzed.

For every message received at the return value worker service, a return value (e.g., heatmap) may be retrieved from a results bucket, and a computation may be performed. According to an example, after retrieving the heatmap from the results bucket, the heatmap worker service may create a zipped bmp heatmap and JSON metadata and pushing it to the results bucket. According to another example, the heatmap worker service may send the heatmap to the results bucket along with a zipped bmp heatmap and JSON metadata.

Technical aspects disclosed herein may provide or perform any or all of the following features: (i) encryption of data in-transit (e.g., using TLS 1.2+), (ii) storage of data at-rest, (iii), encryption keys stored in a Key Management System (KMS), and/or (iv) full-disk (pre-boot) encryption. Encrypting data in-transit may include any one or any combination of data being transmitted to its services, data transmitted within the ecosystem, and data being transmitted back to users. Storing data at-rest may include storing PHI (e.g., AES-256 encryption). The KMS may be, for example, a secure and resilient service that utilizes hardware modules built to FIPS 140-2 standards. Enforcing full-disk (pre-boot) encryption may include enforcing full-disc encryption of any or all devices where customers' data is treated and received.

Computational pathology detection processes and devices may be provisioned behind a Web Application Firewall (WAF) (e.g., WAF 110 in FIG. 2), which may monitor incoming HTTP traffic and filter unpermitted traffic to protect against malicious attacks (e.g., injections, DDOS, etc.).

For an increased level of security, technical aspects disclosed herein may separate production resources from administrative and development resources. For example, granular access controls may be used to prohibit customer data from leaving the production enclave.

FIG. 8 is an exemplary inference architecture for use with the workflows and platforms described in the present disclosure. Within an inference module, a clinical slide may be ingested to an SNS platform 176. The slide may be sent to a scheduler queue (e.g., simple queue service (SQS)) 177, where an inference may be run. The inference may be sent to and/or additionally received from a scheduler 178. An input may also be sent from an AI module 180, which may be provided on a pod on a G4 node 182 along with a result callback API 184. The AI module 180 may post results to a results S3 bucket 186, or get inputs from an ingestion S3 bucket 188.

The scheduler 178 may additionally start a job, get a job status, and delete a completed job when sending information to a K8 job API 190. The K8 job API 190 may in turn send this information to the AI module 180, depending on the AI module design. The scheduler 178 may additionally coordinate and run states, and send the corresponding information to a scheduler database 192.

From the results S3 bucket 186, an S3 notification event may be sent to an S3 event translator queue 193 (e.g., S3 event translator SQS). The notification event may be sent to and/or additionally received from an S3 event translator 194. The event translator 194 may additionally send an uploaded inference result uploaded to the SNS platform 176.

The AI module 180 may additionally post result uploaded callbacks to the result callback API 184 and/or an additional API 196, which may then send the information to the SNS platform 176. The additional API 196 may be in communication with the AI module 180, the results S3 bucket 186, the results database 181, and the SNS platform 176.

The SNS platform 176 may additionally send an ingested clinical slide to a subscriber queue 177 (e.g., subscriber SQS), which may send an inference result to a subscriber module 181. The subscriber module 181 may write a results index and decisions made, which may be sent to a results database 181. The results database 181 may also receive information from and/or send information to the additional API 196, which may read results index and decisions made. The API 196 may also send the read results to the S3 results bucket 186.

As shown in FIG. 8, the SNS platform 176 may be in communication with (e.g., send information to) the scheduler queue 177 and/or scheduler 178 and the subscriber queue 179 and/or subscriber 181. The SNS platform 176 may be in communication with (e.g., receive information from) the results callback API 184, the scheduler 178, the subscriber 181, and the event translator 194.

As shown in FIG. 9, a device 900 (e.g., scanner 104) may include a central processing unit (CPU) 920. CPU 920 may be any type of processing device including, for example, any type of special purpose or a general-purpose microprocessor device. As will be appreciated by persons skilled in the relevant art, CPU 920 also may be a single processor in a multi-core/multiprocessor system, such system operating alone, or in a cluster of computing devices operating in a cluster or server farm. CPU 920 may be connected to a data communication infrastructure 910, for example a bus, message queue, network, or multi-core message-passing scheme.

Device 900 may also include a main memory 940, for example, random access memory (RAM), and may also include a secondary memory 930. Secondary memory 930, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 930 may include similar means for allowing computer programs or other instructions to be loaded into device 900. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 900.

Device 900 also may include a communications interface ("COM") 1060. Communications interface 960 allows software and data to be transferred between device 900 and external devices. Communications interface 960 may include a model, a network interface (such as an Ethernet card), a communications, a PCMCIA slot and card, or the like. Software and data transferred via communications interface 960 may in the form of signals, which may be electronic, electromagnetic, optical or other signals capable of being received by communications interface 960. These signals may be provided to communications interface 960 via a communications path of device 900, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 900 may also include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Referring to FIGS. 1-9, devices, systems, and methods disclosed herein may identify foci that are suspicious for cancer on digital images of histopathology slides. When concerning morphology is detected, devices, systems, and methods disclosed herein may draw the pathologist's attention to foci suspicious for cancer. Systems disclosed herein may provide a deterministic deep learning model that has been trained with digitized hematoxylin & eosin (H&E) slides seen and diagnosed at, for example, Memorial Sloan Kettering Cancer Center (MSKCC).

In the context of prostate cancer, devices, systems, and methods disclosed herein (e.g., global architecture 100, AI modules or SDKs 3a, 3b, 3c, 3d) may identify, determine, or flag digitized H&E prostate needle biopsy images, or regions thereof, that are suspicious for cancer for pathologist review.

For example, the AI modules or SDKs 3a, 3b, 3c, or 3d may include a prostate cancer detection module 3b. The prostate cancer detection module 3b may analyze digital images of prostate tissue or surrounding areas (e.g., a whole side image or WSI containing digitized H&E prostate biopsy and/or excision images). The prostate cancer detection module 3b may identify or determine whether a received image (and/or which images among received images) is suspicious for cancer, determine and/or provide a location of a point of interest in which nearby tissue has a greatest suspicion for cancer, and determine or calculate a grade or score (e.g., Gleason score) to quantify the WSI, such as a total tumor extent and percentage the WSI. The prostate cancer detection module 3b ay further determine patterns based on the locations of points of interest and/or the scores. The prostate cancer detection module 3b may output any of the identifications, determinations, scores, and/or locations of points of interest. The prostate cancer detection module 3b may generate and/or output an additional image containing a predicted likelihood of cancer and each detected pattern across the entire tissue. FIG. 10A exemplifies an output showing area(s) of interest, and FIG. 10B exemplifies an output of an exemplary quantification.

As another example, the AI modules or SDKs 3a, 3b, 3c, or 3d may include a breast cancer detection module 3c. The breast cancer detection module 3c may analyze digital images of breast tissue or surrounding areas (e.g., a whole side image or WSI containing digitized H&E breast biopsy and excision images). The breast cancer detection module 3c may identify or determine whether a received image (and/or which images among received images) is suspicious for cancer, determine and/or provide a location of a point of interest in which nearby tissue has a greatest suspicion for cancer, and determine or calculate a grade or score (e.g., Gleason score) to quantify the WSI, such as a total tumor extent and percentage the WSI. The breast cancer detection module 3c may further determine patterns based on the locations of points of interest and/or the scores. The breast cancer detection module 3c may output any of the identifications, determinations, scores, and/or locations of points of interest. The breast cancer detection module 3c may generate and/or output an additional image containing a predicted likelihood of cancer and each detected pattern across the entire tissue. FIG. 10C exemplifies an output in the form of a heatmap.

Aspects disclosed herein may enable and/or enhance development of powerful software development kits (SDK), development of tools that enable quick research, easy prototyping and delivery of AI Solutions, an AI-native viewing ecosystem, global distribution capabilities, a vast repository of anonymized digital pathology slide images coming from a variety of clinical partners and other parties, scalable secure storage, and compute infrastructure.

Aspects disclosed herein may provide an AI-native development ecosystem to enhance data storage and archive, AI development, visualization and annotations, and sharing and collaboration.

Aspects disclosed herein may provide distribution, marketplace, analytics, and billing. Technical aspects disclosed herein may provide or enhance automated product analytics, reports on usage and consumption, generation of billing reports, distribution of products across the globe, and access and/or reach to data for research.

Aspects disclosed herein may enhance productization and delivery by enhancing stability, availability and support, security and compliance, inference at scale, and workflow and interoperability.

Aspects disclosed herein may enhance data storage by providing anonymization and PHI removal in Whole Slide Images (WSI), management of data access and logical controls, custom dataset creation and extensive search capabilities, monitoring of upload and download volumes, and sharing of data with and collaboration among external individuals or research groups.

Aspects disclosed herein may enhance AI development by allowing a variety of partners and/or parties to design and develop their own algorithms, by enabling development, testing, and validation, by allowing development locally and leveraging the power of deep learning at scale, by providing or allowing access to state of the art frameworks and libraries, and by utilizing the latest GPU hardware.

Aspects disclosed herein may enhance modifications, visualization, and annotations. Aspects disclosed herein may use or allow others to gain insight when reviewing or analyzing a WSI. Insight may be designed and built with users, and may be AI-native, allowing for a richer experience and easy display of AI results. Technical aspects disclosed herein may provide insight that provides advanced annotation features for pathologists. Technical aspects disclosed herein may provide AI solutions that can be integrated at various stages of the workflow.

Aspects disclosed herein may enhance sharing and collaboration by enhancing collection of feedback from other researchers and scientists around the world and allowing various partners and/or parties to collaborate with clinical institutions to share solutions with pathologists and gather feedback for improvements.

Aspects disclosed herein may enhance workflow and/or interoperability by providing a scanner and image agnostic ecosystem. Data may be automatically ingested into the platform with no manual intervention. Support integration with LIS systems may occur through a RESTful set of APIs.

Aspects disclosed herein may enhance inference at scale by providing a global cloud footprint that enables parties to validate their solutions in various institutions, globally, by providing or enabling deep expertise in productization of medical devices, and by providing granular controls around who gets access to an AI solution.

Aspects disclosed herein may enhance security and compliance by encrypting all data in transit and at-rest. Images may be stored in different buckets or containers for each customer and/or institution. Technical aspects disclosed herein may provide continuous security testing and may actively work toward HIPAA, HITRUST, GDPR, SOC2, SOC3, and ISO 27001 compliance.

Aspects disclosed herein may enhance stability and support by providing a stable and reliable infrastructure with high uptimes.

Aspects disclosed herein may enhance development and training of software development kits (SDKs) and the development and execution of unique, customized, and/or user-designed or third party algorithms.

Aspects disclosed herein may support and/or provide SDKs that may support development in Python, but aspects disclosed herein are not limited to a programming language. Aspects disclosed herein may provide machine learning and deep learning development using the PyTorch library. Aspects disclosed herein may utilize advanced hardware for training.

Aspects disclosed herein may enhance deployment and inference at scale, containerized solutions in Docker containers, and containers provided with WSI for inference and support displaying results. Aspects disclosed herein may leverage the elasticity of the cloud to support all users globally.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples to be considered as exemplary only.

What is claimed is:

1. A computer-implemented method for processing an electronic image corresponding to a medical sample associated with a patient, the method comprising:
    receiving one or more whole slide images of a medical sample associated with a patient into a cloud computing environment, the one or more whole slide images being originated from a first user;
    storing the one or more whole slide images in a first encrypted bucket, the first encrypted bucket being located in a first region;
    receiving, by the cloud computing environment, a selection of one or more artificial intelligence (AI) algorithms;
    applying one or more of the selection of one or more AI algorithms to the one or more whole slide images to perform a task on at least a portion of the one or more whole slide images, the task comprising determining a characteristic of the medical sample in the one or more whole slide images;
    based on the characteristic of the one or more whole slide images, generating metadata associated with the one or more whole slide images;
    storing the metadata in a second encrypted bucket, the second encrypted bucket being stored in the first region;
    receiving a request for the one or more whole slide images and metadata associated with the one or more whole slide images from a user device;
    determining, based on a physical location of the user device, whether the user device is authorized to access information in the first encrypted bucket and the second encrypted bucket; and
    based on the determining whether the user device is authorized to access information, transmitting the one or more whole slide images and metadata to the user device from the first encrypted bucket and the second encrypted bucket.

2. The method of claim 1, wherein the selection of one or more AI algorithms is among a plurality of AI algorithms available in the cloud computing environment.

3. The method of claim 2, wherein at least one of the plurality of AI algorithms was developed by a second user, and at least another of the plurality of AI algorithms was developed by a third user different from the second user.

4. The method of claim 3, wherein the second user is located in a different region than the third user.

5. The method of claim 2, wherein the selection of one or more AI algorithms is based on:
    a request indicating a type of task to be performed,
    a request indicating a type of metadata to be generated,
    a command for a particular AI algorithm,
    additional information or metadata associated with the stored one or more whole slide images,
    one or more rules or policies received by the first user,
    one or more rules or policies associated with the selection of one or more AI algorithms among the plurality of AI algorithms, and/or
    one or more rules or policies received from one or more users, the one or more users having developed the selection of one or more AI algorithms among the plurality of AI algorithms.

6. The method of claim 1, further comprising receiving a request, from a second user, to apply the selection of one or more AI algorithm to perform the task on the one or more whole slide images.

7. The method of claim 1, wherein the selection of one or more AI algorithm intakes supplemental information associated with the one or more whole slide images, the supplemental information comprising generic profile patient, patient history, related slide images, radiology data, molecular data, and/or clinical data.

8. The method of claim 1, further comprising:
    determining one or more rules associated with the second encrypted bucket;
    generating a modified whole slide image and/or modified metadata by performing, based on the one or more rules associated with the second encrypted bucket: (i) removing data from the one or more whole slide images and/or removing at least some of the metadata, and/or (ii) changing data from the one or more whole slide images and/or changing at least some of the metadata; and
    based on the determining whether the user device is authorized to access information, outputting the modified whole slide image and/or the modified metadata to the user device.

9. The method of claim 1, further comprising storing the one or more whole slide images in a first encrypted bucket by performing automatic artificial-intelligence based ingestion of the one or more whole slide images, the one or more whole slide images having been received from the first user.

10. The method of claim 1, wherein determining whether the user device is authorized to access information includes determining that the user device is associated with a same institution as the first user.

11. The method of claim 1, wherein applying the selection of one or more artificial intelligence algorithm to perform the task is performed based on patient metadata associated with the patient.

12. The method of claim 1, wherein generating metadata further comprises:
    determining a heatmap, the heatmap comprising a graphical prediction of a likelihood of an attribute in the medical sample.

13. A system for processing an electronic image corresponding to a medical sample associated with a patient, the system comprising:
    at least one memory storing instructions; and at least one processor configured to execute the instructions to perform operations comprising:

receiving one or more whole slide images of a medical sample associated with a patient into a cloud computing environment, the one or more whole slide images being originated from a first user;

storing the one or more whole slide images in a first encrypted bucket, the first encrypted bucket being located in a first region;

receiving, by the cloud computing environment, a selection of one or more artificial intelligence (AI) algorithms;

applying one or more of the selection of one or more AI algorithms to the one or more whole slide images to perform a task on at least a portion of the one or more whole slide images, the task comprising determining a characteristic of the medical sample in the one or more whole slide images;

based on the characteristic of the one or more whole slide images, generating metadata associated with the one or more whole slide images;

storing the metadata in a second encrypted bucket, the second encrypted bucket being stored in the first region;

receiving a request for the one or more whole slide images and metadata associated with the one or more whole slide images from a user device;

determining, based on a physical location of the user device, whether the user device is authorized to access information in the first encrypted bucket and the second encrypted bucket; and based on the determining whether the user device is authorized to access information, transmitting the one or more whole slide images and metadata to the user device from the first encrypted bucket and the second encrypted bucket.

14. The system of claim 13, wherein the selection of one or more AI algorithms is among a plurality of AI algorithms available in the cloud computing environment, at least one of the plurality of AI algorithms was developed by a second user, and at least another of the plurality of AI algorithms was developed by a third user different from the second user.

15. The system of claim 14, wherein the selection of one or more AI algorithms is based on:

a request indicating a type of task to be performed,
a request indicating a type of metadata to be generated,
a command for a particular AI algorithm,
additional information or metadata associated with the stored one or more whole slide images,
one or more rules or policies received by the first user,
one or more rules or policies associated with the selection of one or more AI algorithms among the plurality of AI algorithms, and/or
one or more rules or policies received from one or more users, the one or more users having developed the selection of one or more AI algorithms among the plurality of AI algorithms.

16. A non-transitory computer-readable medium storing instructions that, when executed by a processor, cause the processor to perform operations for processing an electronic image corresponding to a medical sample associated with a patient, the operations comprising:

receiving one or more whole slide images of a medical sample associated with a patient into a cloud computing environment, the one or more whole slide images being originated from a first user;

storing the one or more whole slide images in a first encrypted bucket, the first encrypted bucket being located in a first region;

receiving, by the cloud computing environment, a selection of one or more artificial intelligence (AI) algorithms;

applying one or more of the selection of one or more AI algorithms to the one or more whole slide images to perform a task on at least a portion of the one or more whole slide images, the task comprising determining a characteristic of the medical sample in the one or more whole slide images;

based on the characteristic of the one or more whole slide images, generating metadata associated with the one or more whole slide images;

storing the metadata in a second encrypted bucket, the second encrypted bucket being stored in the first region;

receiving a request for the one or more whole slide images and metadata associated with the one or more whole slide images from a user device;

determining, based on a physical location of the user device, whether the user device is authorized to access information in the first encrypted bucket and the second encrypted bucket; and based on the determining whether the user device is authorized to access information, transmitting the one or more whole slide images and metadata to the user device from the first encrypted bucket and the second encrypted bucket.

17. The non-transitory computer-readable medium of claim 16, wherein the selection of one or more AI algorithms is among a plurality of AI algorithms available in the cloud computing environment, at least one of the plurality of AI algorithms was developed by a second user, and at least another of the plurality of AI algorithms was developed by a third user different from the second user.

* * * * *